United States Patent [19]

Weingarten

[11] Patent Number: 4,602,012
[45] Date of Patent: Jul. 22, 1986

[54] CEPHALOSPORIN ANTIBIOTICS

[75] Inventor: Gordon G. Weingarten, London, England

[73] Assignee: Glaxo Group Limited, London, England

[21] Appl. No.: 688,354

[22] Filed: Jan. 2, 1985

[30] Foreign Application Priority Data

Jan. 3, 1984 [GB] United Kingdom ................. 8400024

[51] Int. Cl.$^4$ ................... A61K 31/545; C07D 501/34
[52] U.S. Cl. ........................................ 514/202; 544/22
[58] Field of Search ........................... 544/22; 514/202

[56] References Cited

U.S. PATENT DOCUMENTS

| 3,935,204 | 1/1976 | Dahlén | 544/22 |
| 4,267,320 | 5/1981 | Gregson | 544/22 |
| 4,446,317 | 5/1984 | Gregson et al. | 544/22 |

Primary Examiner—Donald G. Daus
Assistant Examiner—Robert Benson
Attorney, Agent, or Firm—Bacon & Thomas

[57] ABSTRACT

There are described compounds of formula (I)

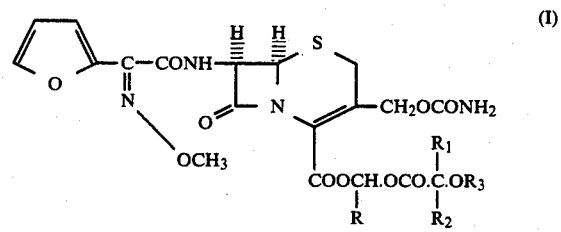

wherein R, $R_1$ and $R_2$ which may be the same or different, each represents a hydrogen atom or a $C_{1-4}$ alkyl group and $R_3$ represents a $C_{1-4}$ alkyl group with the proviso that, when both $R_1$ and $R_2$ represent hydrogen atoms, $R_3$ represents other than a methyl group. These cefuroxime esters are valuable as providing orally administrable forms of the antibiotic cefuroxime. Methods of preparing cefuroxime esters, pharmaceutical compositions containing the esters and methods for their use in medicine are also described.

Novel intermediates for use in the preparation of the cefuroxime esters are also described.

7 Claims, No Drawings

CEPHALOSPORIN ANTIBIOTICS

This invention is concerned with improvements in or relating to cephalosporin antibiotics. More particularly the invention is concerned with esters of (6R, 7R)-3-carbamoyloxymethyl-7-[(Z)-2-(fur-2-yl)-2-methoxyiminoacetamido]ceph-3-em-4-carboxylic acid (i.e. the syn isomer), which has the approved name 'cefuroxime'.

Cefuroxime, as disclosed in GB No. 1453049, is a valuable broad spectrum antibiotic characterised by high activity against a wide range of gram-positive and gram-negative microorganisms, this property being enhanced by the very high stability of the compound to $\beta$-lactamases produced by a range of gram-positive and gram-negative microorganisms. It is well tolerated in the mammalian body and is widely used as an antibiotic in clinical practice.

Cefuroxime and its salts are principally of value as injectable antibiotics since they are poorly absorbed from the gastro-intestinal tract and are therefore present in sera and urine in only low concentrations after oral administration. Extensive studies into the result of administering various derivatives of cefuroxime by the oral route have accordingly been conducted in the knowledge tht the development of derivatives which are absorbed from the gastro-intestinal tract and are converted in the body into the present antibiotic following oral administration will extend still further the valuable therapeutic use of cefuroxime.

It is known from the literature pertaining to $\beta$-lactam antibiotics that the absorption from the gastro-intestinal tract following oral administration of certain penicillin and cephalosporin antibiotics may be improved (compared with the parent antibiotic) by converting the free 3-carboxy group in the case of penicillin compounds, or the free 4-carboxy group in the case of cephalosporin compounds, into particular esterified carboxy groups. The presence of an appropriate esterifying group can thus enhance absorption of the parent antibiotic from the gastro-intestinal tract, but as the ester per se has little or no antibacterial activity it is important that after absorption it is rapidly converted into the antibacterial parent acid. Thus the ester group should be sufficiently susceptible to enzymatic hydrolysis after absorption, but on the other hand it is necessary that the ester should be sufficiently stable to reach the site of absorption without undergoing significant degradation in the alimentary tract. Absorption of the ester is also dependent upon an acceptable combination of aqueous and lipid solubilities. The precise nature of the esterifying group is therefore critical if this delicate balance of properties is to be achieved.

Various esters of cefuroxime have been described as potentially useful for oral administration. For example GB No. 1572993 describes acyloxymethyl esters, GB No. 1571683 describes other acyloxyalkyl esters and GB No. 1598568 describes alkoxycarbonyloxyalkyl esters of cefuroxime. Because of the delicate balance of properties required for such esters the search for new esters having a particularly desirable combination of properties for oral administration has continued.

Two esters of cefuroxime amongst the many which have been subjected to preliminary testing and evaluation are the pivaloyloxymethyl and pivaloyloxyethyl esters. As referred to in, for example, GB No. 1571683, the pivaloyloxymethyl ester of ampicillin is known to improve the oral absorption of ampicillin but it was found that the pivaloyloxymethyl ester of cefuroxime exhibits little effect upon oral administration. The pivaloyloxymethyl ester, although well absorbed in some animal species, exhibited insufficient absorption for therapeutic use when administered to humans. In consequence the pivaloyloxymethyl (and pivaloyloxyethyl) esters of cefuroxime have hitherto been of little interest.

The present invention has been made following a better understanding of the properties of the pivaloyloxymethyl and pivaloyloxyethyl esters of cefuroxime. It has thus now been established that these esters have the very desirable property of good stability to esterases present in the intestinal lumen and thus when administered orally are capable of reaching the site of absorption without undergoing significant degradation. On the other hand these esters have relatively low aqueous solubility and are insufficiently absorbed for use in human medicine. It is thought that the good stability to esterases present in the intestinal lumen is due to the blocking effect of the bulky pivaloyl moiety present in these esters and attempts have been made to improve aqueous solubility, and thus absorption, by introducing polar functionality whilst maintaining the bulk of the ester group, e.g. by replacing one of the hydrogen atoms of the pivaloyl moiety by a hydroxy or methoxy group. Compounds of this type which have been prepared and tested in vivo have however given uniformly poor results.

It has now surprisingly been discovered that compounds in which one of the methyl groups of the pivaloyl moiety is replaced by a $C_{1-4}$ alkoxy group combine good stability to esterases present in the lumen with good aqueous solubility and absorption from the gastro-intestinal tract. Thus, despite the discouraging results previously obtained for the pivaloyloxymethyl and pivaloyloxyethyl esters of cefuroxime, it has been established in accordance with the present invention that related esters have a combination of properties which is especially desirable for oral administration. It has further been established that other related esters in which one or both of the remaining methyl groups of the pivaloyl moiety are replaced by hydrogen or $C_{2-4}$ alkyl groups similarly have a desirable combination of properties for oral administration.

According to the invention there are thus provided compounds of formula (I)

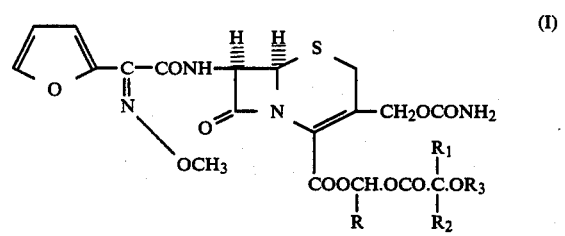

wherein R, $R_1$ and $R_2$, which may be the same or different, each represents a hydrogen atom or a $C_{1-4}$ alkyl group and $R_3$ represents a $C_{1-4}$ alkyl group, with the proviso that, when both $R_1$ and $R_2$ represent hydrogen atoms, $R_3$ represents other than a methyl group. Individual diastereoisomers of the ester group and mixtures thereof are embraced by the invention.

As explained above, the compounds according to the invention possess a desirable combination of properties for oral administration and are thus valuable as providing orally administrable forms of the antibiotic cefuroxime. In particular the esters (I) possess adequate stability including stability to esterases present in the intestinal lumen so that upon oral administration they can reach the intestinal mucosa without substantial degradation occurring, have a good combination of aqueous and lipid solubilities so that they are well absorbed from the gastro-intestinal tract and after absorption are hydrolyzed by esterases present in body tissues and blood leading to formation of the valuable broad spectrum antibiotic cefuroxime.

The compounds of the invention may be used for treating a variety of diseases caused by pathogenic bacteria in human beings and animals, such as respiratory tract and urinary tract infections.

Preferred compounds of formula (I) as defined above are those in which R represents a hydrogen atom or a methyl group, $R_1$ and $R_2$ each represents a methyl group and $R_3$ represents a $C_{1-4}$ alkyl group, particularly a methyl group.

Particularly preferred compounds of the invention by virtue of their especially favourable properties include:
(R and S)1-(2-methoxy-2-methylpropionyloxy)ethyl (6R,7R)-3-carbamoyloxymethyl-7-[(Z)-2-(fur-2-yl)-2-methoxyiminoacetamido]ceph-3-em-4-carboxylate (Compound A) and diastereoisomeric mixtures thereof and
(2-methoxy-2-methylpropionyloxy)methyl (6R,7R)-3-carbamoyloxymethyl-7-[(Z)-2-(fur-2-yl)-2-methoxyiminoacetamido]ceph-3-em-4-carboxylate (Compound B).

The compounds of formula (I) wherein $R_1$ and $R_2$ are hydrogen atoms and $R_3$ represents a methyl group have too high toxicity to be potentially useful for oral administration and are therefore not included within the scope of the invention.

Compound A has been subjected to very extensive evaluation. It has been found to possess to a strong degree the desirable combination of properties for oral administration which are characteristic of the compounds according to the invention, namely adequate stability including good stability to esterases present in the intestinal lumen, a good combination of aqueous and lipid solubilities so that is is well absorbed from the gastro-intestinal tract and susceptibility to hydrolysis after absorption. As regards the degree of absorption of Compound A, the results of a study carried out on human volunteers show an average oral absorption of greater than 50% with values for individual subjects generally being within the range of from 40% to 60%. This represents a high and consistent degree of absorption, the consistency of absorption being an important property for clinical use. Compound A has good stability to gut enzymes and it is believed that the consistency of absorption is attributable at least in part to this. Compound A can be readily prepared by precipitation in a highly pure, amorphous form suitable for pharmaceutical formulation. Also Compound A has an acceptable taste for formulation in paediatric suspensions.

Compound B has also been subjected to a very extensive evaluation and has in general been found to possess similar advantageous properties to Compound A.

According to a further feature of the invention we provide a process for the preparation of the cefuroxime esters of formula (I) which comprises either
(A) esterifying a compound of formula (II)

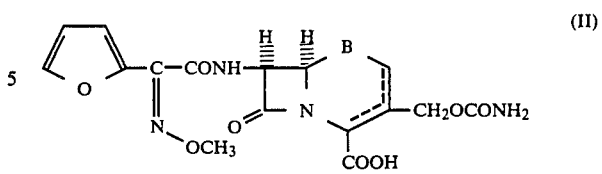

(wherein B is >S or >S→O; and the dotted line bridging the 2-, 3- and 4-positions indicates that the compound is a ceph-2-em or ceph-3-em compound) or a salt thereof, e.g. an alkali metal salt (such as the sodium or potassium salt) or an onium salt, e.g. an ammonium salt (such as a quaternary ammonium salt), or a 3-N-carbamoyl protected derivative thereof, with a compound of formula (III)

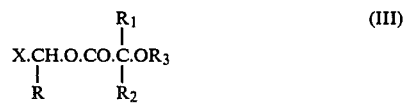

(wherein R, $R_1$, $R_2$ and $R_3$ are as defined above; and X is a leaving group, e.g. a halogen atom such as chlorine, bromine or iodine or an acyloxy group, e.g. a hydrocarbylsulphonyloxy group such as mesyloxy or tosyloxy, or a haloalkanoyloxy group such as a dichloroacetoxy group); or (B) acylating a compound of formula (IV)

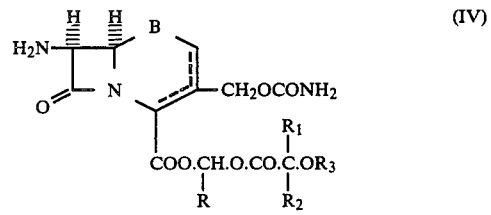

(wherein R, $R_1$, $R_2$, $R_3$, B and the dotted line are as hereinbefore defined) or a salt thereof, e.g. an acid addition salt (formed with, for example, a mineral acid such as hydrochloric, hydrobromic, sulphuric, nitric or phosphoric acid or an organic acid such as methanesulphonic or toluene-p-sulphonic acid) or a 7-N-silyl derivative thereof, or a 3-N-carbamoyl-protected derivative thereof, with an acid of formula (V)

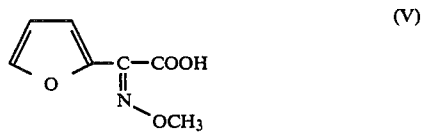

or with an acylating agent corresponding thereto; or
(C) reacting a compound of formula (VI)

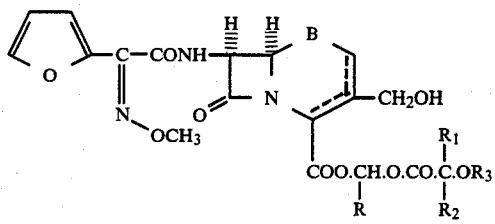

(wherein R, R₁, R₂, R₃, B and the dotted line are as hereinbefore defined) with a suitable carbamoylating agent; or (D) oximating a compound of formula (VII)

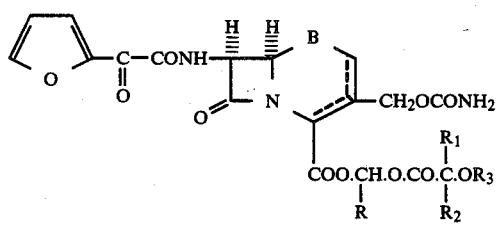

(wherein R, R₁, R₂, R₃, B and the dotted line are as hereinbefore defined) or a 3-N-carbamoyl-protected derivative thereof by reaction with methoxyamine of formula (VIII)

or a salt thereof; or (E) methylating a compound of formula (IX)

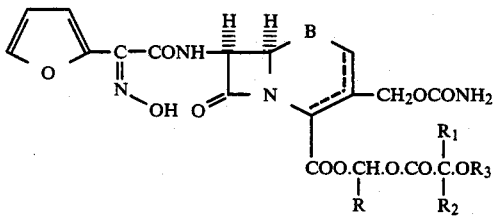

(wherein R, R₁, R₂, R₃, B and the dotted line are as hereinafter defined) or a 3-N-carbamoyl-protected derivative thereof by reaction with a methylating agent, e.g. diazomethane, dimethyl sulphate or a compound of formula (X)

wherein Y represents a leaving group, e.g. a halogen atom such as chlorine, bromine or iodine or an acyloxy group, e.g. a hydrocarbylsulphonyloxy group such as mesyloxy or tosyloxy, or a haloalkanoyloxy group such as a dichloroacetoxy group); or (F) alkylating a compound of formula (XI)

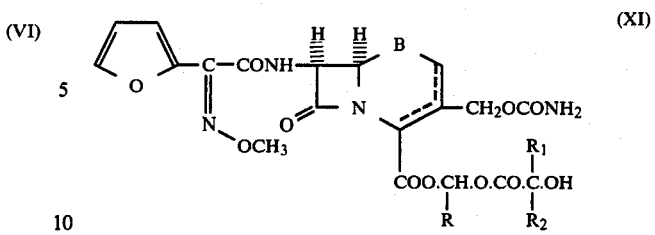

(wherein R, R₁, R₂, B and the dotted line are as hereinbefore defined) or a 3-N-carbamoyl-protected derivative thereof by reaction with a suitable alkylating agent, e.g. a diazoalkane, a dialkyl (e.g. dimethyl) sulphate, a trialkyl orthoformate or a compound of formula (XII)

$$R_3Y \quad (XII)$$

wherein $R_3$ is as hereinbefore defined; and Y represents a leaving group, e.g. a halogen atom such as chlorine, bromine or iodine or an acyloxy group, e.g. a hydrocarbylsulphonyloxy group such as mesyloxy or tosyloxy, or a haloalkanoyloxy group such as a dichloroacetoxy group); or (G) isomerization of a compound of formula (XIII)

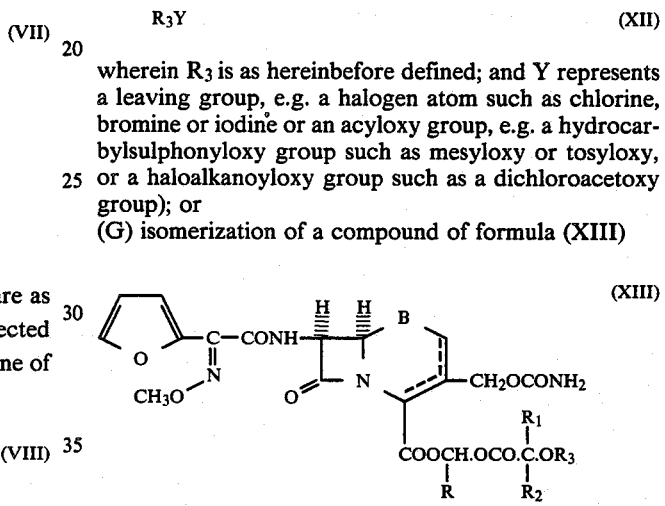

(wherein R, R₁, R₂, R₃, B and the dotted line are as hereinbefore defined) or a 3-N-carbamoyl-protected derivative thereof:

following which, if necessary and/or desired in each instance, any of the following steps, in any appropriate sequence, are carried out (i) conversion of a ceph-2-em isomer into the desired ceph-3-em isomer, (ii) reduction of a compound wherein B is >S→O to form a compound wherein B is >S, (iii) removal of any N-protecting groups, or (iv) as a final step, recovering a compound of formula (I) in substantially amorphous form from a solution thereof.

In the above-described processes, the cephalosporin starting materials of formulae (II), (IV), (VI), (VII), (IX), (XI) and (XIII) are preferably compounds wherein B is >S and the dotted line represents ceph-3-em compounds.

Process (A) is conveniently effected in solution in an inert organic solvent. Suitable organic solvents include amides e.g. an N,N-disubstituted amide such as N,N-dimethylformamide, N,N-dimethylacetamide or hexamethylphosphoric triamide; ketones such as acetone; sulphoxides such as dimethylsulphoxide; nitriles such as acetonitrile; or liquid sulphur dioxide. The reaction may be carried out at a temperature in the range −50° to +150° C., e.g. −10° to +50° C., conveniently between −10° C. and +30° C. When a cefuroxime salt, for example, the sodium salt, is employed as starting material and the reaction is effected in, for example, a nitrile solvent, a crown ether such as 15-crown-5 may, if desired, be employed. Where cefuroxime free acid is employed as starting material, the esterification is conducted in the presence of a base. Suitable bases for use in the esterification include e.g. inorganic bases such as sodium carbonate or potassium carbonate. It is convenient to add the base to the cefuroxime-containing reaction system prior to addition of the compound (III).

It is convenient to employ substantially equivalent amounts of cefuroxime and base, e.g. about 0.5 moles of a diacidic base such as potassium carbonate per mole of cefuroxime. The use of a compound (III) in which X is bromine or iodine has been found advantageous in that under these conditions the formation of a ceph-2-em ester product is kept to a minimum.

The above-described starting materials of formula (II) may be prepared in conventional manner, for example by the methods described in GB No. 1453049.

The starting materials of formula (III) may be prepared in conventional manner. For example, compounds of formula (III) wherein X represents a halogen atom may be prepared by reaction of a compound of formula (XIV)

(XIV)

(wherein $R_1$, $R_2$ and $R_3$ are as defined above and $X^1$ represents a halogen atom such as bromine or chlorine) with an aldehyde of formula R CHO in the presence of a Lewis acid catalyst such as zinc chloride or aluminium chloride. The reaction may conveniently be carried out in an organic solvent such as a halogenated hydrocarbon e.g. dichloromethane and chloroform, and conveniently at a temperature of from $-10°$ to $+10°$ C.

Compounds of formula (III) wherein X represents a halogen atom and R represents a methyl group may also be prepared by reaction of a compound of formula (XV)

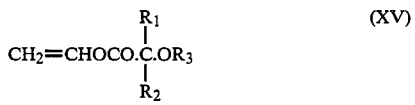

(XV)

(wherein $R_1$, $R_2$ and $R_3$ are as hereinbefore defined) with a hydrogen halide such as hydrogen bromide or hydrogen chloride. The reaction may if desired be carried out in the presence of an organic solvent, for example, a halogenated hydrocarbon such as chloroform, and conveniently at a temperature of from $-20°$ to $+30°$ C.

Compounds of formula (III) may also be prepared by halogen-exchange; for example a compound in which X is iodo may be prepared from the corresponding chloro- or bromo-compound using an iodide salt such as sodium iodide.

The starting materials of formula (III) are novel compounds and as such provide a further feature of the present invention.

Acylating agents which may be employed in process (B) for the preparation of compounds of formula (I) include acid halides, particularly acid chlorides or bromides. Such acylating agents may be prepared by reacting an acid of formula (V) or salt thereof with a halogenating agent e.g. phosphorus pentachloride, thionyl chloride or oxalyl chloride. Acylations employing acid halides may be effected in aqueous and non-aqueous reaction media, and conveniently at temperatures of from $-50°$ to $+50°$ C., preferably $-20°$ to $+30°$ C.

Suitable reaction media include aqueous ketones such as aqueous acetone, aqueous alcohols such as aqueous ethanol, esters such as ethyl acetate, halogenated hydrocarbons such as methylene chloride, amides such as dimethylacetamide, nitriles such as acetonitrile, or mixtures of two or more such solvents.

Acylation with an acid halide may be effected in the presence of an acid binding agent (e.g. a tertiary amine such as triethylamine or dimethylaniline, an inorganic base such as calcium carbonate or sodium bicarbonate, or an oxirane, preferably a lower-1,2-alkylene oxide such as ethylene oxide or propylene oxide) which serves to bind hydrogen halide liberated in the acylation reaction.

The free acid of formula (V) may itself be used as the acylating agent. Such acylations are desirably conducted in the presence of a condensing agent, for example a carbodiimide such as N,N'-dicyclohexylcarbodiimide; a carbonyl compound such as carbonyldiimidazole; or an isoxazolium salt such as N-ethyl-5-phenylisoxazolium-3'-sulphonate or N-t-butyl-5-methylisoxazolium perchlorate. The condensation reaction is desirably effected in an anhydrous reaction medium, such as a halogenated hydrocarbon (e.g. methylene chloride), an amide (e.g. dimethylformamide), a nitrile (e.g. acetonitrile) or an ether (e.g. tetrahydrofuran).

Acylation may also be effected with other derivatives of acids of formula (V), such as an activated ester. An activated ester may conveniently be formed in situ using for example 1-hydroxybenzotriazole in the presence of a condensing agent for example N,N'-dicyclohexylcarbodiimide.

Acylation may also be effected with other amide-forming derivatives of the acid of formula (V) such as, for example, a symmetrical anhydride or a mixed anhydride, e.g. formed with pivalic acid or with a haloformate such as a lower alkyl haloformate. The mixed or symmetrical anhydrides may be produced in situ. Thus, for example, a mixed anhydride may be produced using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example toluene-p-sulphonic acid).

An alternative method involves reacting an acid of formula (V) with a solution or suspension preformed by adding a carbonyl halide, in particular oxalyl chloride or phosgene, or a phosphoryl halide such as phosphorus oxychloride to a solvent such as a halogenated hydrocarbon, for example methylene chloride, containing a lower acyl tertiary amide such as N,N-dimethylformamide. The activated form of the acid of formula (V) may then be reacted with a compound of formula (IV) in a suitable solvent or mixture of solvents, for example an alkanol such as an alcohol, e.g. aqueous ethanol or aqueous industrial methylated spirits. The acylation reaction may conveniently be effected at temperatures of from $-50°$ to $+50°$ C., preferably $-40°$ to $+30°$ C., if desired in the presence of an acid binding agent, for example triethylamine.

If desired, the above acylation reactions may be carried out in the presence of a catalyst such as 4-dimethylaminopyridine.

The above-described starting materials of formula (IV) may be prepared in conventional manner, for example using the techniques described in U.S. Pat. No. 3,905,963, GB No. 1041985 and DOS No. 2818025, or by esterification of the corresponding free acid using the methods described above.

Carbamoylation of 3-hydroxymethyl compounds of formula (VI) according to process (C) may be effected by conventional methods using suitable carbamoylating agents, for example isocyanates of formula $R_4$.NCO (wherein $R_4$ is a labile substituent group) to give a compound containing a 3-position substituent having the formula $-CH_2O.CONHR_4$ (wherein $R_4$ has the above defined meaning). The carbamoylation reaction may desirably be effected in the presence of a solvent or solvent mixture selected from hydrocarbons (e.g. aromatic hydrocarbons such as benzene and toluene), halogenated hydrocarbons (e.g. dichloromethane), amides (e.g. formamide or dimethylformamide), esters (e.g. ethyl acetate), ethers (e.g. cyclic ethers such as tetrahydrofuran and dioxan), ketones (e.g. acetone), sulphoxides (e.g. dimethylsulphoxide) and mixtures of these solvents. The reaction may conveniently be carried out at a temperature of between $-80°$ C. and the boiling temperature of the reaction mixture, for example up to 100° C., preferably between $-20°$ and $+30°$ C. The labile group $R_4$ may subsequently be cleaved, e.g. by hydrolysis, to form a 3-carbamoyloxymethyl group. Examples of labile groups $R_4$ which are readily cleavable upon subsequent treatment include an acyl group, especially a lower alkanoyl group such as acetyl, a halo-substituted lower alkanoyl group such as mono-, di- or trichloroacetyl, a chlorosulphonyl or bromosulphonyl group, a halogenated alkoxycarbonyl group such as 2,2,2-trichloroethoxycarbonyl or a trimethylsilyl group. Such labile groups may generally be cleaved by acid or base catalysed hydrolysis (e.g. by base catalysed hydrolysis using sodium bicarbonate). Halogenated groups such as chlorosulphonyl, dichlorophosphoryl, trichloroacetyl and 2,2,2-trichloroethoxycarbonyl may also be cleaved reductively, while groups such as chloroacetyl may also be cleaved by treatment with thioamides such as thiourea.

The carbamoylating agent is desirably used in excess for example at least 1.1 moles relative to the compound of formula (VI). The carbamoylation may be assisted by the presence of a base, e.g. a tertiary organic base such as a tri-(lower alkyl)amine (e.g. triethylamine) or by employing the compound (VI) in the form of an alkali metal (e.g. sodium) salt, although such assistance may not be necessary in the case of more active isocyanates, e.g. compounds in which $R_4$ is a strongly electron-withdrawing group such as chlorosulphonyl or trichloroacetyl. Carbamoylations involving reaction of an ester of formula (VI) with excess isocyanate wherein $R_4$ is a group such as chlorosulphonyl or trichloroacetyl are thus of particular practical advantage by virtue of the simplicity of the reaction conditions, since there is no need for temporary blocking and subsequent deblocking of the 4-position carboxy group of the cephalosporin and since the electron-withdrawing $R_4$ group in the resulting N-protected 3-carbamoyloxymethyl cephalosporin product is readily removed by, for example, hydrolysis with aqueous sodium bicarbonate.

It should be noted that it may be convenient to retain or even introduce an N-substituting group $R_4$ during transformations of intermediate 3-carbamoyloxymethyl compounds in order to minimise unwanted side reactions involving the carbamoyloxymethyl group.

Another useful carbamoylating agent is cyanic acid, which is conveniently generated in situ, for example, from an alkali metal cyanate such as sodium cyanate, the reaction being facilitated by the presence of an acid, e.g. a strong organic acid such as trifluoroacetic acid. Cyanic acid effectively corresponds to the isocyanate compounds mentioned above wherein $R_4$ is hydrogen and therefore converts compounds of formula (VI) directly to their 3-carbamoyloxymethyl analogues.

Alternatively, carbamoylation may be effected by reaction of the compound of formula (VI) with phosgene or carbonyldiimidazole followed by ammonia or the appropriate substituted amine, optionally in an aqueous or non-aqueous reaction medium.

The above described starting materials of formula (VI) may be prepared in situ by the esterification of the corresponding 4-carboxylic acid or a salt thereof (e.g. an alkali metal salt such as the sodium or potassium salt) with a compound of formula (III) as described above except that a temperature in the range $-100°$ C. to $+150°$ C., conveniently between $-70°$ C. to $+30°$ C., is preferably employed.

The oximation reaction according to process (D) may be effected in aqueous or non-aqueous reaction media, conveniently at a temperature in the range $-20°$ to $+100°$ C., e.g. $-10°$ to $+50°$ C., preferably about $0°$ C. It is convenient to use methoxyamine in the form of a salt, for example an acid addition salt such as the hydrochloride. When such a salt is employed the reaction is conveniently carried out in the presence of an acid binding agent e.g. an organic base such as pyridine.

Solvents which may be employed include water, alcohols (e.g. methanol or ethanol), amides (e.g. N,N-dimethylformamide, N,N-dimethylacetamide or hexamethylphosphoramide), ethers (e.g. cyclic ethers such as tetrahydrofuran or dioxan, and acyclic ethers such as dimethoxyethane or diethylether), nitriles (e.g. acetonitrile), nitroalkanes (e.g. nitromethane), sulphoxides (e.g. dimethylsulphoxide), sulphones (e.g. sulpholane), hydrocarbons such as halogenated hydrocarbons (e.g. methylene chloride), and esters such as ethyl acetate, as well as mixtures of two or more such solvents.

When aqueous conditions are employed the reaction may conveniently be effected at a pH in the range from 2.0 to 9.0, preferably from 3 to 8. The pH may conveniently be maintained in this range by the addition of an appropriate acid or base, for example a mineral acid such as hydrochloric or sulphuric acid or an alkali metal carbonate or bicarbonate e.g. sodium bicarbonate.

The starting materials of formula (VII) are novel compounds and as such provide a further feature of the present invention. They may be prepared by an acylation reaction analogous to process method (B) above from a compound of formula (IV) and fur-2-ylglyoxylic acid or an acylating agent corresponding thereto.

Where in the reaction according to process (E) diazomethane is used as the methylating agent, the reaction may conveniently be effected in an organic medium, for example in cyclic or acylic ethers (e.g. tetrahydrofuran, dioxan, diethyl ether or diglyme), amides (e.g. N,N-dimethylformamide, N,N-dimethylacetamide or hexamethylphosphoramide), nitriles (e.g. acetonitrile), esters (e.g. ethyl acetate), halogenated hydrocarbons (e.g.

methylene chloride) or hydrocarbons (e.g. benzene) as well as in mixtures of such solvents. The reaction is conveniently carried out at from −50° to +50° C., preferably 0° to 30° C., optionally in the presence of a Lewis acid, e.g. $BF_3$ conveniently in the form of a solvate, e.g. an etherate.

Examples of reaction media which may be employed when dimethyl sulphate or a compound of formula (X) is used as methylating agent include any of those referred to above in relation to the use of diazomethane above, or additionally lower ketones (e.g. acetone), nitroalkanes (e.g. nitromethane), sulphoxides (e.g. dimethylsulphoxide) and sulphones (e.g. sulpholane), as well as mixtures of such solvents. The reaction medium may contain some water, but is preferably anhydrous. The reaction may conveniently be effected at a temperature in the range −50° to +100° C., preferably 0° to 50° C.

The compounds of formula (IX), which are used as starting materials for the methylation may be prepared by the esterification, in a manner analogous to process method (A) above, of the corresponding free 4-carboxylic acid. Such acids may be prepared by processes as described in GB No. 1389194. The compounds of formula (IX) and the corresponding free 4-carboxylic acids are novel compounds, and as such provide a yet further feature of the present invention.

The alkylation reaction according to process (F) is conveniently effected in an inert organic solvent. When a diazoalkane is used as the alkylating agent, suitable solvents and reaction temperatures and optional Lewis acids are as described above for the use of diazomethane as methylating agent in process (E), e.g. $BF_3$ etherate in dichloromethane/diethylether, or aluminium chloride in ether. Similarly where a dialkyl (e.g. dimethyl) sulphate, a trialkyl orthoformate or a compound of formula (XII) is used as the alkylating agent, suitable solvents and reaction temperatures are as described above for the use of dimethyl sulphate or a compound of formula (X) as methylating agent in process (E). If a trialkyl orthoformate is used as alkylating agent, reaction is preferably carried out in the presence of a strong acid, such as sulphuric acid or perchloric acid. If a compound of formula (XII) is used as alkylating agent, reaction is preferably carried out in the presence of a base, such as an alkali metal hydroxide or carbonate e.g. caustic soda or sodium carbonate.

The compounds of formula (XI) which are used as starting materials for the alkylation may be prepared by the esterification of the corresponding 4-carboxylic acid in a manner analagous to process method (A) above. The hydroxy group in the esterifying agent may be protected during the esterification reaction, for example by using an esterifying agent in the form of an ester. Tetrahydropyran-2-yl is one suitable protecting group.

The compounds of formula (XI) and the corresponding free acids are novel compounds and as such provide a yet still further feature of the present invention.

The isomerisation reaction according to process (G) is conveniently effected in an inert organic solvent, using U.V. light desirably at a wavelength in excess of 290 nm. Suitable solvents include nitriles (e.g. acetonitrile), alcohols (e.g. t-butanol) or ethers (e.g. tetrahydrofuran). The isomerisation may conveniently be carried out at a temperature in the range 0° to 100° C., preferably between 10° and 30° C.

A ceph-2-em ester derivative obtained in accordance with any of the processes of the invention may be converted into the corresponding ceph-3-em derivative by, for example, treatment of the ceph-2-em ester with a base, such as pyridine or triethylamine.

If the desired ceph-3-em ester product is significantly contaminated by the corresponding ceph-2-em isomer the product may be oxidised (e.g. by treatment with a peracid such as metaperiodic acid, peracetic acid, monoperphthalic acid or m-chloroperbenzoic acid or with t-butyl hypochlorite in the presence of a weak base such as pyridine) to give the ceph-3-em 1-oxide ester, which may then be reduced as described hereinafter to yield substantially pure ceph-3-em ester.

Where a compound is obtained in which B is >S→O this may be converted into the corresponding sulphide by, for example, reduction of the corresponding acyloxysulphonium or alkoxysulphonium salt prepared in situ by reaction with e.g. acetyl chloride in the case of an acetoxysulphonium salt, reduction being affected by, for example, sodium dithionite or by iodide ion as in a solution of potassium iodide in a solvent e.g. acetic acid, acetone, tetrahydrofuran, dioxan, dimethylformamide or dimethylacetamide. The reaction may be effected at a temperature from −50° to +50° C., preferably −20° to +20° C.

Suitable N-carbamoyl-protecting groups which may be employed during the processes described above include e.g. an acyl group such as acetyl, a halo-substituted lower alkanoyl group such as a mono-, di- or tri-chloroacetyl or chlorosulphonyl group, or a trimethylsilyl group. Such protecting groups may be cleaved by acid- or base-catalysed hydrolysis. The halogenated groups may also be cleaved reductively, while groups such as dichloroacetyl may also be cleaved by treatment with thioamides.

The compounds of formula (I) may be readily prepared in highly pure amorphous form essentially free of crystalline material. Techniques which may be employed to recover amorphous compounds of formula (I) include those wherein the product is precipitated from solution and those wherein solvent is removed from the solution, preferably rapidly, and the product deposited. Methods involving the use of these procedures which have been found satisfactory include solvent precipitation, freeze drying, spray drying and roller drying.

Solvent precipitation is the preferred technique for preparing amorphous compounds of formula (I). When employing solvent precipitation, suitable solvents from which the compounds of formula (I) may be precipitated include ketones (e.g. acetone), alcohols (e.g. methanol or ethanol, if desired in the form of methylated spirits (e.g. IMS)), acetonitrile, tetrahydrofuran, dioxan, esters (e.g. methyl or ethyl acetate), chlorinated solvents (e.g. dichloromethane or chloroform), and mixtures thereof, if desired with other solvents (e.g. water, where this gives a homogeneous phase). Precipitation may be effected by mixing with appropriate quantities of a non-solvent for the compounds. Suitable non-solvents include water, alkanes and mixtures of alkanes (e.g. hexane or medium boiling range petrol (e.g. 60°–80° C.)), ethers (e.g. isopropyl ether) or aromatic hydrocarbons (e.g. benzene or toluene). The solvent and non-solvent should be compatible i.e. they should be at least partially miscible and preferably fully miscible. Typical combinations of solvent and non-solvent are dichloromethane/isopropyl ether, ethyl acetate/petrol, ethyl acetate/isopropyl ether, acetone/water and methanol/water. The solid should be removed from solution as quickly as possible and dried as quickly as possible to avoid formation of any crystalline material. As an aid to rapid recovery a carrier gas e.g. air may be bubbled through the solution.

The technique of solvent precipitation may usefully be applied to the reaction mixture remaining after an esterification reaction in which the compounds of formula (I) have been formed in order to obtain the amorphous compounds directly. This may be achieved by mixing the reaction mixture with a solvent e.g. an ester such as ethyl acetate and an appropriate non-solvent, e.g. petrol, or by diluting the reaction mixture with water.

Residual solvent may be present in the final product in varying amounts immediately after precipitation. This can, if necessary, be removed by further treatment, e.g. by drying under vacuum.

According to a still further aspect of the present invention there are provided pharmaceutical compositions for oral administration comprising a compound of formula (I) as hereinbefore defined in association with at least one pharmaceutical carrier or excipient.

The pharmaceutical compositions according to the invention may take the form of, for example, tablets or capsules prepared by conventional means with pharmaceutically acceptable excipients such as binding agents (e.g. pregelatinised maize starch, polyvinyl-pyrrolidone or hydroxypropyl-methyl-cellulose), fillers (e.g. starch, lactose, micro-crystalline cellulose or calcium phosphates), lubricants (e.g. magnesium stearate, hydrogenated vegetable oils, talc, silica, polyethyleneglycols), disintegrants (e.g. potato starch or sodium starch glycolate), or wetting agents (e.g. sodium lauryl sulphate). Flow aids e.g. silicon dioxide may also be used if desired. The tablets may be coated by methods well known in the art.

Liquid preparations for oral administration may take the form of, for example, solutions, syrups or suspensions, or they may be presented as a dry product either for constitution with water or other suitable vehicle before use for administration as a liquid, or for direct administration and then washed down with water or other suitable liquid. Such liquid preparations may be prepared by conventional means with pharmaceutically acceptable additives such as suspending agents (e.g. sorbitol syrup, methyl cellulose or hydrogenated edible fats and oils such as hydrogenated castor oil), emulsifying or thickening agents (e.g. lecithin, aluminium stearates or acacia), non-aqueous vehicles (e.g. almond oil, fractionated coconut oil, oily esters or ethyl alcohol), preservatives (e.g. methyl or butyl p-hydroxybenzoates or sorbic acid) and suitable flavouring and sweetening agents.

The compositions according to the invention may contain between 0.1-99% of the active ingredient, conveniently from 30-95% for tablets and capsules and 3-50% for liquid preparations. Compositions in dosage unit form conveniently contain 50 to 500 mg of the active ingredient per dosage unit. Doses employed for human treatment will typically be in the range of 100 to 3000 mg per day, e.g. 250 to 2,000 mg per day for adults and 125 to 1,000 mg per day for children, although the precise dose will depend on, inter alia, the frequency of administration.

In a yet further feature of the present invention we provide a method of combating bacterial infections of the human or animal body which comprises orally administering thereto an effective amount of a compound of formula (I) as hereinbefore defined.

The following Examples illustrate the present invention.

All temperatures are quoted in °C.

Cefuroxime is the approved name for (6R,7R)-3-carbamoyloxymethyl-7-[(Z)-2-(fur-2-yl)-2-methoxyiminoacetamido]ceph-3-em-4-carboxylic acid.

Petroleum ether refers to the fractions boiling between 40° C. and 80° C.

Unless otherwise stated, u.v. spectra were determined in ethanol, i.r. spectra in bromoform, optical rotations were measured as a 1% solution in ethyl acetate, PMR spectra were recorded on a 60 MHz or 100 MHz spectrometer and the following abbreviations are used: s=singlet, d=doublet, tr=triplet, q=quartet.

INTERMEDIATE 1

1,1-Dimethylethoxyacetyl Chloride 1,1-Dimethylethoxyacetic acid (13.2 g) was dissolved in 1N aqueous methanolic sodium hydroxide solution (100 ml). The solution was concentrated under reduced pressure and evaporated to dryness by azeotroping off the water with toluene (2×100 ml). The resulting sodium salt was dried over phosphorus pentoxide under vacuum overnight. Anhydrous ether (300 ml) and N,N-dimethylformamide (0.2 ml) were added and a solution of redistilled oxalyl chloride (8.5 ml) in anhydrous ether (50 ml) was added dropwise over 30 mins. causing the solvent to reflux gently. The mixture was stirred for 5 hrs. filtered, concentrated on a rotary evaporator to give a liquid (13.5 g) which was distilled under reduced pressure to give the title acid chloride (3.24 g); b.p. 58°-60°/22 mm Hg.

INTERMEDIATE 2

Ethoxyacetyl Bromide

To a solution of ethoxyacetic acid (20.82 g) in anhydrous petroleum ether (100 ml) cooled to 0° was added phosphorus tribromide (22.19 g) dropwise. The cooling bath was removed and the solution was stirred for 3 hrs. The layers were then separated and the lower layer was extracted several times with petroleum ether. The petroleum ether solutions were combined, the solvent was evaporated and the liquid obtained was distilled under reduced pressure to give the title acid bromide (29.4 g); b.p. 72°/54 mm Hg.

INTERMEDIATE 3

2-Methoxy-2-methylpropanoic Acid Ethenyl Ester

A mixture of 2-methoxy-2-methylpropanoic acid (5.9 g), vinyl acetate (5 ml), mercuric acetate (172 mg), palladium acetate (27 mg) and potassium hydroxide (225 mg) was stirred under nitrogen at ca 50° for 4 hours. More vinyl acetate (10 ml) was added and the reaction was allowed to proceed for a further 18½ hours. The mixture was cooled to 2° and N aqueous sodium hydroxide (45 ml) was added. The layers were separated and the aqueous layer was extracted with ether (50 ml). The combined organic layers were washed with saturated brine (20 ml), dried over magnesium sulphate and concentrated on a rotary evaporator to give a yellow liquid (4.44 g) which was distilled under reduced pressure to give the title ethenyl ester (2.52 g); b.p. 43°-45°/ca 20 mm Hg.

INTERMEDIATE 4

(Novel compounds of formula (III))

(a) 2-Methoxy-2-methylpropanoic Acid Chloromethyl Ester

2-Methoxy-2-methylpropanoic acid (2.36 g) and powdered potassium carbonate (1.38 g) were stirred in anhydrous N,N-dimethylformamide (50 ml) for 17 hrs. Chloroiodomethane (7.06 g) was added and the mixture was stirred for a further 2½ hours. It was poured into water (200 ml) and the aqueous solution was extracted with ether (2×200 ml). The combined organic phases were washed sequentially with 2N hydrochloric acid (3×60 ml), water (50 ml), saturated aqueous sodium bicarbonate (70 ml), water (2×60 ml) and saturated brine (50 ml), dried over magnesium sulphate and the solvent was evaporated off to give an oil (1.4 g). PMR showed this to be an approximately 2:3 mixture of the Chloromethyl ester and di(2-methoxy-2-methylpropionyloxy)methane; $\tau(CDCl_3)$ 4.12 (s, $-CO_2)_2CH_2$), 4.23 (s, $CH_2Cl$), 6.72 (s, $OCH_3$) and 8.56 (s, $C(CH_3)_2$); $\nu(CHBr_3)$ 1760 cm$^{-1}$ (ester C=O).

(b) 2-Methoxy-2-methylpropanoic Acid Iodomethyl Ester

A solution of crude 2-methoxy-2-methylpropanoic acid chloromethyl ester (1.36 g) and sodium iodide (4.5 g) in acetone was heated under reflux for 50 mins. The solvent was evaporated off and the residue was partitioned between 20% aqueous sodium metabisulphite solution (20 ml) and ether 3×50 ml). The organic layers were combined, washed with saturated brine (20 ml), dried over magnesium sulphate and evaporated under reduced pressure to give an oil (1.56 g). PMR showed this to be an approximately 2:3 mixture of the iodomethyl ester and di(2-methoxy-2-methylpropionyloxy)methane; $\tau(CDCl_3)$ 4.02 (s, $CH_2I$), 4.12 (s, $(-CO_2)_2CH_2$), 6.70 (s,$CH_3O$), 8.55 (s, $C(CH_3)_2$ in the iodomethyl ester) and 8.56 (s, $C(CH_3)_2$ in the acylal); $\nu$max (CHBr) 1750 cm$^{-1}$ (ester C=O).

INTERMEDIATE 5

(Novel compound of formula (III))

(R and S) Ethoxyacetic Acid 1-Bromethyl Ester

To a solution of ethoxyacetyl bromide (24.3 g) in anhydrous dichloromethane (60 ml) containing zinc chloride (100 mg), stirred under dry nitrogen at $-5°$, was added a solution of acetaldehyde (12.3 ml) in dichloromethane (20 ml) dropwise over 20 mins. The solution was stirred at $-5°$ for 45 mins and was then allowed to warm up to $10°$. Cold dichloromethane (100 ml) was added and the solution was filtered through neutral alumina and evaporated under reduced pressure without heating the flask, to give the bromoethyl ester as a brown oil (19.7 g), $\tau(CDCl_3)$ 3.26 (t, J 6 Hz, CHBr), 5.90 (s, $CH_2$), 6.40 (q, J 7 Hz, $OCH_2CH_3$), 8.01 (d, J 6 Hz, $CHCH_3$), 8.76 (t, J 7 Hz, $OCH_2CH_3$).

INTERMEDIATE 6

(Novel compound of formula (III))

(R and S) Ethoxyacetic Acid 1-Bromo-2-Methylpropyl Ester

To a solution of ethoxyacetyl bromide (3.0 g) in anhydrous dichloromethane (15 ml) containing zinc chloride (50 mg), stirred under dry nitrogen at $-4°$, was added a solution of redistilled 2-methylpropanal (2.45 ml) in dichloromethane (5 ml) dropwise over 10 mins. The solution was stirred at $-4'$ for 1 hour and was then allowed to warm up to $10°$. The solution was filtered through neutral silica gel and was concentrated under reduced pressure without heating to give the ester as a dark oil (3.42 g), $\tau(CDCl_3)$ 3.45 (d, J 5 Hz, CHBr), 6.40 (q, J 7 Hz, $OCH_2CH_3$), 7.9 (m, $CH(CH_3)_2$). 8.76 (t, J 7 Hz, $OCH_2CH_3$), 8.95 (d, J 6 Hz, $C(CH_3)_2$).

INTERMEDIATE 7

(Novel compound of formula (III))

(R and S) 2-Methoxy-2-methylpropanoic Acid 1-Bromoethyl Ester

Hydrogen bromide was bubbled into 2-methoxy-2-methylpropanoic acid ethenyl ester (3.03 g) cooled in an ice/IMS bath for 7 mins. Excess hydrogen bromide was blown out with nitrogen and the product was distilled under water-pump pressure (ca 20 mm Hg) to give the title 1-bromoethyl ester (2.86 g); b.p. $86°-88°$.

INTERMEDIATE 8

(Novel compound of formula (III))

2-Methoxypropanoic Acid 1-Bromoethyl Ester

A slow stream of hydrogen bromide was passed onto an ice-cooled solution of 2-methoxypropanoic acid ethenyl ester (2.9 g) in chloroform (15 ml) for 10 mins. Excess hydrogen bromide was removed in a stream of nitrogen and the solution was dried over sodium sulphate and evaporated under reduced pressure to give the title 1-bromoethyl ester (4.05 g); $\tau(CDCl_3)$ 3.21 (q, J 6 Hz, CHBr), 6.08 (q, J 7 Hz, CH $OCH_3$), 6.58 (s,)$CH_3$), 7.97 (d, J 6 Hz, $CH_3$ CHBr) and 8.60 (d, J 7 Hz, $CH_3$ CH $OCH_3$).

INTERMEDIATE 9

(Novel compound of formula (III))

(R and S) 1,1-Dimethylethoxyacetic Acid 1-Chloroethyl Ester

To a solution of 1,1-dimethyethoxyacetyl chloride (3.33 g) in anhydrous dichloromethane (30 ml) containing zinc chloride (120 mg) and stirred under nitrogen in an ice/IMS bath was added a solution of acetaldehyde (1.5 ml) in dichloromethane (10 ml) over 5 mins. The cooling bath was removed and the reaction mixture was stirred for 5½ hours. The solution was filtered through neutral alumina (2.5 g) and evaporated under reduced pressure to give the title 1-chloroethyl ester as a liquid (3.13 g); $\nu$max (CS$_2$) 1765 cm$^{-1}$ (C=O); $\tau(CDCl_3)$ 3.42 (q, J 5 Hz, CHCl), 5.95 (s, $CH_2$) 8.39 (d, J 5 Hz, $CH_3CH$) and 8.74 (s, $C(CH_3)_3$).

INTERMEDIATE 10

(6R,7R)-7-(2-Thienylacetamido)-3-(trichloroacetylcarbamoyloxymethyl)ceph-3-em-4-carboxylic Acid Trichloroacetylisocyanate (4.3 ml) was added rapidly to a stirred suspension of (6R,7R)-3-hydroxymethyl-7-(2-thienylacetamido)ceph-3-em-4-carboxylic acid (10.62 g) at $6°$ in ethyl acetate (70 ml). The reaction mixture was stirred at $5°$ for 40 min. Petroleum ether was added dropwise during 15 min. The mixture was stirred for 30 min, filtered and the solid was washed with petroleum ether and dried to give the title compound as a solid (16.48 g), $[\alpha]_D^{22}+73°$ (c 1.2 in Me$_2$SO).

INTERMEDIATE 11

(R and S) 1-(2-Methoxy-2-methylpropionyloxy)ethyl (6R,7R)-7-(2-Thienylacetamido)-3-(trichloroacetylcarbamoyloxymethyl)ceph-3-em-4-carboxylate A solution of Intermediate 10 (8.075 g) in dimethylformamide (75 ml) was stirred with powdered potassium carbonate (1.035 g), for 50 min at 20°. The solution was cooled and stirred at 4° and treated rapidly with Intermediate 7 (4.50 g). It was stirred at 4° for 1 h, then at 22° for 2 h 35 min, and was poured into ethyl acetate (300 ml) and 2M-hydrochloric acid (100 ml). The aqueous layer was extracted with ethyl acetate (3×50 ml), and the combined organic layers were washed with 2M-hydrochloric acid (100 ml), water (100 ml), saturated sodium bicarbonate solution (100 ml), water (100 ml) and brine (2×100 ml). The organic layer was dried over magnesium sulphate and was evaporated to a foam. This foam was dissolved in ethyl acetate (40 ml) and the precipitate which formed was removed by filtration. The filtrate was added with stirring to petroleum ether (600 ml) to give the title compound as a solid (5.72 g), $[\alpha]_D^{22}+47°$ (c 1.1 in CHCl$_3$).

INTERMEDIATE 12

(R and S) 1-(2-Methoxy-2-methylpropionyloxy)ethyl (6R,7R)-7-Amino-3-(trichloroacetylcarbamoyloxymethyl)ceph-3-em-4-carboxylate Pyridine (1.30 ml) was added to a stirred solution of phosphorus pentachloride (3.34 g) in dichloromethane (40 ml) under nitrogen at 3°. The temperature rose to 8°. The mixture was cooled to 4° and treated with Intermediate 11 (4.5 g) during 5 min. The solution was stirred at ca. 0° for 1 h 20 min and added under nitrogen to a stirred solution of methanol (7 ml) in dichloromethane (14 ml) at −40°. The resulting solution was stirred for 30 min, warming to −5°, when water (20 ml) was added. This mixture was stirred at ca. −5° for 1.5 h, then at 15° for 30 min. The aqueous layer was separated and extracted with dichloromethane (2×50 ml). The organic layers were combined and washed with saturated sodium bicarbonate (50 ml), water (50 ml), and brine (50 ml). The solution was dried, concentrated to ca. 20 ml, and added to petroleum ether (200 ml). The precipitate was washed and dried to give the title compound as a solid (3.00 g), $\lambda_{max}$ 258.5 nm ($E_1^1$ 111).

INTERMEDIATE 13

(R and S) 1-(2-Methoxy-2-methylpropionyloxy)ethyl (6R,7R)-7-Amino-3-carbamoyloxymethylceph-3-em-4-carboxylate A solution of Intermediate 12 (2.8 g) in methanol (40 ml) was stirred with a solution of sodium formate (0.834 g) in water (10 ml) at 20° for 2 h. Sodium formate (0.3 g) was added and the solution was stirred at 20° for a further 2.5 h. The solution was concentrated and poured into ethyl acetate (100 ml) and sodium bicarbonate solution (50 ml). The aqueous layer was extracted with ethyl acetate and the organic layers were combined and washed with water (100 ml) then brine (100 ml), dried over magnesium sulphate and evaporated to give an oil. This oil was dissolved in ethyl acetate (20 ml) and the solution was added to petroleum ether (200 ml) to give a precipitate which was washed and dried to give the title compound (1.33 g) as a solid, $\lambda_{max}$ 257.5 nm ($E_1^1$ 136).

INTERMEDIATE 14

Potassium (6R,7R)-7-[(Z)-2-(Fur-2-yl)-2-methoxyiminoacetamido]-3-hydroxymethylceph-3-em-4-carboxylate A solution of (6R,7R) 7-[(Z)-2-(fur-2-yl)-2-methoxyiminoacetamido]-3-hydroxymethylceph-3-em-4-carboxylic acid (10.038 g) in ethanol (150 ml) at ca. 40° was clarified by filtering through kieselguhr. The filtrate was treated dropwise with a 0.5M-solution of potassium acetate (52.6 ml) over 20 min. The crystallising mixture was cooled to 4° during 1.5 h and was filtered. The solid was washed with ethanol (3×40 ml) then ether (2×40 ml) and was dried at ca. 1 mm Hg and 20° over phosphorus pentoxide for 20 h to give the title compound (11.11 g), $[\alpha]_D^{20}+65°$ (c 1.2 in H$_2$O).

INTERMEDIATE 15

(R and S) 1-(2-Methoxy-2-methylpropionyloxy)ethyl (6R,7R)-3-Hydroxymethyl-7-[(Z)-2-(fur-2-yl)-2-methoxyiminoacetamido]ceph-3-em-4-carboxylate A suspension of Intermediate 14 (4.213 g) in dimethylformamide (200 ml) was cooled to −4° under nitrogen. Intermediate 7 (3.067 g) was added with stirring and the temperature rose briefly to 6°. The mixture was cooled to −5° and stirred at −5° for 15 min, then at 0° for a further 70 min. This solution of the title compound was used without characterisation.

INTERMEDIATE 16

(R and S) 1-(2-Methoxy-2-methylpropionyloxy)ethyl (6R,7R)-3-trichloroacetylcarbamoyloxymethyl-7-[(Z)-2(fur-2-yl)-2-methoxyiminoacetamido]ceph-3-em-4-carboxylate A solution of Intermediate 15 in dimethyl formamide (100 ml) was stirred at 0° under nitrogen with trichloroacetyl isocyanate (3.44 ml). The temperature rose to 10°. The mixture was cooled to 5° during 5 min and was poured into a stirred mixture of ice (200 ml) 2M-hydrochloric acid (400 ml) and ethyl acetate (200 ml). The aqueous layer was extracted with more ethyl acetate (200 ml) and the organic layers were combined and washed with 2M-hydrochloric acid (2×100 ml), water (3×100 ml; but still acidic), and brine (2×100 ml; still acidic). The organic layer was dried, concentrated to ca. 30 ml and added to petroleum ether (400 ml) to give the title compound as a solid (2.373 g). A portion (1.50 g) was purified by dissolving in ethyl acetate cooled to −20° filtered and washed. The filtrates were combined, diluted with ethyl acetate (50 ml) washed with saturated sodium bicarbonate solution (30 ml), water (2×30 ml), brine (30 ml) and dried. The solution was concentrated to ca. 15 ml and added to petroleum ether (300 ml) to give the title compound, $\lambda_{max}$ 275 nm ($E_1^1$ 307).

INTERMEDIATE 17

Potassium (4R,6R,7R)-3-Hydroxymethyl-7-(2-thienylacetamido)-ceph-2-em-4-carboxylate A solution of (4R,6R,7R)-3-hydroxymethyl-7-(2-thienylacetamido)ceph-2-em-4-carboxylic acid (5.064 g) in ethanol (150 ml) at ca. 40° was filtered and treated dropwise with stirring with a solution of potassium acetate (1.417 g) in ethanol (10 ml). A solid crystallised and the mixture was stirred at 20° for 2 h and filtered.

The solid was washed and dried to give the title compound (4.927 g), m.p. 222°–240° (decomp.).

INTERMEDIATE 18

(R and S) 1-(2-Methoxy-2-methylpropionyloxy)ethyl (6R,7R)-3-Carbamoyloxymethyl-7-[(E)-2-(fur-2-yl)-2-methoxyiminoacetamido]ceph-3-em-4-carboxylate A solution of the 1-(2-methoxy-2-methylpropionyloxy)ethyl ester of cefuroxime (8.528 g) in toluene (250 ml) was stirred with 2-mercaptobenzothiazole (12.5 g) at reflux for 24 h. It was cooled to 22° and allowed to stand for 24 h, giving crystals which were filtered off. The filtrate was evaporated to give a foam (6.10 ). Part (6.0 g) of this foam was chromatographed on a column of Kieselgel 60 (70–230 mesh; 600 g) made up in ethyl acetate-dichloromethane (1:4). The column was eluted with dichloromethane containing increasing amounts of ethyl acetate to give fractions which were combined and evaporated to an oil. The oil was dissolved in ethyl acetate (25 ml) which was added to petroleum ethyl (400 ml) to give the title compound as a solid (2.594 g), $\nu_{max}$ 276 nm ($E_1^1$ 293).

INTERMEDIATE 19

(R and S) 1-(2-Methoxy-2-methylpropionyloxy)ethyl (4R,6R,7R)-7-(2-Thienylacetamido)-3-(trichloroacetylcarbamoylmethyl)ceph-2-em-4-carboxylate A solution of Intermediate 17 (4.00 g) in dimethylformamide (200 ml) was cooled to 0° with stirring under nitrogen. Intermediate 7 (2.98 g) was added and the mixture was stirred at between 0° and 6° for 1.65 h. The mixture was cooled to −4° and was treated with trichloroacetylisocyanate (1.5 ml) at between −4° and 1°. The mixture was stirred at −4° for 15 min, then at 8° for 1 h. The mixture was poured into ethyl acetate (400 ml) and 2M-hydrochloric acid (200 ml). The aqueous layer was extracted with ethyl acetate (2×1509 ml). The organic layers were combined and washed with 2M-hydrochloric acid (150 ml), water (200 ml), saturated sodium bicarbonate solution (2×150 ml), and brine (2×150 ml). The solution was dried over magnesium sulphate, concentrated to ca. 25 ml and filtered. The filtrate was added to isopropyl ether (400 ml) to give the title compound as a solid (2.015 g), $[\alpha]_D^{22}$ +208° (c 1.2 in CHCl$_3$).

INTERMEDIATE 20

(R and S) 1-(2-Methoxy-2-methylpropionyloxy)ethyl (4R,6R,7R)-7-Amino-3-(trichloroacetylcarbamoylmethyl)ceph-2-em-4-carboxylate Pyridine (0.56 ml) was added to a solution of phosphorus pentachloride (1.44 g) in dichloromethane (20 ml) at 4° under nitrogen at ca. 4°. Intermediate 19 (1.90 g) was added to the suspension over 5 min. The solution was stirred at ca. 0° for 15 min., then at −5°, warming to 10° during 2 h. The mixture was then cooled to −5° and added under nitrogen to a solution of methanol (3.5 ml) in dichloromethane (7 ml) at −40° to −20°. The reaction mixture was stirred at −5° for 30 min; water (10 ml) was added and the mixture was stirred at −5° to −3° for 1.5 h. The mixture was warmed to 15° and the aqueous layer was separated and extracted with dichloromethane. The organic layers were combined, washed with saturated sodium bicarbonate solution (25 ml), water (25 ml), and brine (25 ml). The solution was dried over magnesium sulphate, concentrated to ca. 10 ml, and added to isopropyl ether (100 ml) to give the title compound as a solid (0.795 g), $\lambda_{max}$ 251 nm ($E_1^1$ 122).

INTERMEDIATE 21

(R and S) 1-(2-Methoxy-2-methylpropionyloxy)ethyl (4R,6R,7R)-7-Amino-3-carbamoyloxymethylceph-2-em-4-carboxylate A solution of Intermediate 20 (0.700 g) in methanol (10 ml) was stirred with a solution of sodium formate (0.208 g) in water (3 ml) for 2 h at 22°. More sodium formate (69 mg, 1.0 mmol) was added and the solution was stirred for a further 1 h at 22°. The solution was concentrated and the product was shaken with ethyl acetate (25 ml) and saturated sodium bicarbonate solution (15 ml). The aqueous layer was extracted with ethyl acetate (2×20 ml). The organic layers were combined, washed with water (20 ml), then brine (20 ml) and the solution was dried over magnesium sulphate and evaporated to an oil. The oil was redried at ca. 1 mm Hg and 22° to give the title compound as a foam (437 mg), $\lambda_{max}$ 224.5 mm ($E_1^1$ 175), $\lambda_{infl}$ 245 nm ($E_1^1$ 128) $\lambda_{max}$ 290.5 nm ($E_1^1$ 20).

INTERMEDIATE 22

(R and S) 1-(2-Methoxy-2-methylpropionyloxy)ethyl (4R,6R,7R)-3-Carbamoyloxymethyl-7-[(Z)-2-(fur-2-yl)-2-methoxyiminoacetamido]ceph-2-em-4-carboxylate A mixture of Intermediate 21 (400 mg) and (Z)-2-(fur-2-yl)-2-methoxyiminoacetic acid (171 mg) in dichloromethane (15 ml) was stirred with dicyclohexylcarbodiimide (230 mg) for 1 h at 22°. Acetic acid (two drops) was added and the solid was filtered off and washed. The filtrate was evaporated then partitioned between ethyl acetate (50 ml) and saturated sodium bicarbonate solution (15 ml). The organic layer was washed with water (2×15 ml) and brine (15 ml), and was dried over magnesium sulphate and evaporated to give an oil (490 mg). This product was adsorbed on silica (2.5 g) and chromatographed on a column of silica (50 g) made up in dichloromethane-ethyl acetate (3:1). Dichloromethane-ethyl acetate (3:1) eluted a small amount of non polar material. Dichloromethane-ethyl acetate (2:1) eluted fractions which were combined and evaporated to give the title compound as a solid (22 mg), $[\alpha]_D^{22}$ +286°.

INTERMEDIATE 23

(R and S) 1-(2-Methoxy-2-methylpropionyloxy)ethyl (1S,6R,7R)-3-Carbamoyloxymethyl-7-[(Z)-2-(fur-2-yl)-2-methoxyiminoacetamido]ceph-3-em-4-carboxylate-1-oxide (i) A solution of Intermediate 22 (14 mg) and m-chloroperbenzoic acid (4.9 mg of 85%) in dichloromethane (2 ml) was stirred at 0° to 4° for 1 h. The solution was evaporated and the solid was triturated with ether to give the title compound as a solid (8 mg), $\nu_{max}$ (Nujol) 3385, 3270, and 3200 (NH, NH$_2$), 1788 ($\beta$-lactam), 1745 and 1730 (CO$_2$R), 1698 (probably OCONH$_2$), 1660 and 1530 cm$^{-1}$ (CONH).

(ii) A solution of Intermediate 22 (containing ca. 25% of the $\Delta^3$ isomer: 1.144 g) and m-chloroperbenzoic acid (497 mg of 85%) in dichloromethane (30 ml) was stirred at 20° for 1 h. The solution was washed with sodium metabisulphite solution, sodium bicarbonate solution, water and brine. It was diluted with ethyl acetate, dried and evaporated to give the title compound as a solid (0.84 g), $[\alpha]_D^{21} +46°$.

INTERMEDIATE 24

Diphenylmethyl (6R,7R)-3-Carbamoyloxymethyl-7-[(fur-2-yl)glyoxamido]-ceph-3-em-4-carboxylate Diphenylmethyl (6R,7R)-7-amino-3-carbamoyloxymethylceph-3-em-4-carboxylate toluene-p-sulphonic acid alt (4.28 g) was dissolved in ethyl acetate (200 ml) and sodium bicarbonate solution (200 ml). The ethyl acetate layer was separated, washed with water, dried over magnesium sulphate and cooled to 0°. To this solution were added ethyl acetate solutions of dicyclohexylcarbodimide (1.46 g) and 2-furylglyoxalic acid (991 mg). The reaction mixture was stirred at 0° for 20 minutes, filtered and the filtrate was evaporated in vacuo. Trituration of the residue with ethanol give the title compound (3.53 g) m.p. 169°-171°.

INTERMEDIATE 25

(6R,7R)-3-Carbamoyloxymethyl-7-[(fur-2-yl)glyoxamido]ceph-3-em-4-carboxylic acid Trifluoroacetic acid (5.5 ml) was added to a cold (0°) stirred mixture of anisole (5.5 ml) and Intermediate 24 (1.84 g). After ten minutes, the reaction mixture was poured into aqueous sodium bicarbonate (100 ml) and ethyl acetate (100 ml). The aqueous layer was separated, washed with ethyl acetate (100 ml) and acidified to pH 2 under ethyl acetate. Insoluble material was filtered off and combined with the solid obtained after washing, drying (MgSO4) and evaporating the ethyl acetate layer. The product was crystallised from methanol to give the title compound (678 mg) $[\alpha]_D^{22} +64°$ (c, 0.988 in aqueous sodium bicarbonate).

INTERMEDIATE 26

(Novel compound of formula (VII)) (R and S) 1-(2-Methoxy-2-methylpropionyloxy)ethyl (6R,7R)-3-Carbamoyloxymethyl-7-[(fur-2-yl)glyoxamido]ceph-3-em-4-carboxylate A solution of (6R,7R)-3-carbamoyloxy methyl-7-[(fur-2-yl)glyoxamido]ceph-3-em-4-carboxylic acid (3.00 g) in dimethylformamide (30 ml) was stirred with potassium carbonate (0.524 g) at 22° for 1 h under nitrogen. The solution was cooled to ca. 0° and stirred with Intermediate 7 (1.88 g) at 0° to 4° for 2.5 h. The reaction mixture was poured into ethyl acetate (200 ml) and 2M-hydrochloric acid (100 ml), and the aqueous layer was separated and extracted with ethyl acetate (2×50 ml). The organic layers were combined and washed with 2M-hydrochloric acid (50 ml), water (100 ml), saturated sodium bicarbonate solution (2×100 ml), and brine, and the solution was dried over magnesium sulphate. The solution was concentrated to ca. 30 ml and added to petroleum ether (300 ml) to give the title compound as a solid (2.940 g), $[\alpha]_D^{22} +107°$ (c 0.94 in CHCl3).

INTERMEDIATE 27

(6R,7R)-3-Carbamoyloxymethyl-7-[(Z)-2-[fur-2-yl)-2-hydroxyiminoacetamido]ceph-3-em-4-carboxylic Acid A suspension of (Z)-2-(fur-2-yl)-2-hydroxyiminoacetic acid (3.00 g) in dichloromethane (100 ml) at 10° was stirred with 2-methoxypropene (10 ml). The solution formed was then stirred at ca. 22° for 15 min. and evaporated to an oil. This oil was redissolved in dichloromethane (100 ml) and stirred at 22° with methoxypropane (5 ml) for 15 min. The solution was evaporated and the oil was dissolved in dichloromethane (50 ml) to give a solution of the protected acid.

Oxalylchloride (1.85 ml) was added to a solution of dimethylformamide (1.9 ml) in dichloromethane (40 ml) with stirring under nitrogen at −20°. The mixture was stirred at ca. 0° for 10 min, then cooled to −20° and stirred with the solution of the protected acid from above. This mixture was stirred at ca. 0° for 10 min, cooled to −20° and added to a solution of (6R,7R)-7-amino-3-carbamoyloxymethylceph-3-em-4-carboxylic acid (5.465 g) and triethylamine (8 ml) in industrial methylated spirit (40 ml) and water (12 ml) at ca. 0°. The mixture was stirred, warming to 22° over 25 min. It was poured into dichloromethane (300 ml) and water (50 ml) and the aqueous layer was washed with dichloromethane (2×100 ml). The aqueous layer was allowed to stand at 22° and pH 8 for ca. 2 h. The pH was adjusted to 1.5 with 2M-hydrochloric acid, and the mixture was extracted with ethyl acetate (4×200 ml). The organic layers were combined and washed with 2M-hydrochloric acid (100 ml), water (100 ml) and brine. The solution was dried over magnesium sulphate and evaporated to give a foam, which was triturated with ether to give the title compound as a solid (4.115 g), $\lambda_{max}$ 270.5 nm ($E_1^1$ 420).

INTERMEDIATE 28

(Novel compound of formula (IX))

(R and S) 1-(2-Methoxy-2-methylpropionyloxy)ethyl (6R,7R)-3-Carbamoyloxymethyl-7-[(Z)-2-(fur-2-yl)-2-hydroxyiminoacetamido]ceph-3-em-4-carboxylate A solution of Intermediate 27 (1.00 g) in dimethylformamide (20 ml) was stirred with potassium carbonate (168 mg) at 22° under nitrogen for 1 h. This mixture was then stirred at 0° to 4° with Intermediate 7 (0.822 g) for 90 min and poured into ethyl acetate (100 ml) and 2M-hydrochloric acid (50 ml). The aqueous layer was separated and extracted with ethyl acetate (2×50 ml). The organic layers were combined and washed with 2M-hydrochloric acid (50 ml), water (100 ml), saturated sodium bicarbonate (3×30 ml), and brine (50 ml). The solution was dried over magnesium sulphate, concentrated to ca. 15 ml and added to petroleum ether (200 ml) to give the title compound as a solid (0.617 g), $[\alpha]_D +38°$ (c 1.1).

INTERMEDIATE 29

Chloromethyl (2-Hydroxy-2-methyl)propionate (2-Hydroxy-2-methyl)propanoic acid (5.20 g) was dissolved in 40% aqueous tetra n-butyl ammonium hydroxide (31 ml) and the solution was azeotroped with toluene (6×100 ml). The resulting oil was dried under vacuum and dissolved in chloroform (250 ml). Iodochloromethane (17.65 g) was added and the solution was left at 22° for 112 hours. The solution was evaporated under reduced pressure and the resulting oil was stirred with petrol (3×50 ml). The residual crystals were triturated with ether (2×100 ml). The ether solutions were evaporated to give an oil (2.41 g) that was stirred with petrol (2×50 ml) and the petrol was evaporated to give the chloromethyl ester (0.37 g).

INTERMEDIATE 30

Iodomethyl (2-Hydroxy-2-methyl)propionate

A solution of Intermediate 29 (1.0 g) and sodium iodide (3 g) in acetone (50 ml) was heated under reflux for 50 mins. The solvent was evaporated off and the residue was partitioned between 20% aqueous sodium metabisulphite solution (20 ml) and chloroform (2×50 ml). The organic layers were combined, washed with saturated brine (20 ml), dried over magnesium sulphate and evaporated under reduced pressure to give the title compound as an oil (0.89 g) $\nu_{max}$ 3540 (OH) and 1742 cm$^{-1}$ (ester C=O).

INTERMEDIATE 31

(Novel compound of formula (XI))

(2-Hydroxy-2-methylpropionyloxy)methyl (6R,7R)-3-Carbamoyloxymethyl-7-[(Z)-2-(fur-2-yl)-2-methoxyiminoacetamido]ceph-3-em-4-carboxylate Cefuroxime (1.697 g) and powdered potassium carbonate (276 mg) were stirred in N,N-dimethylformamide (20 ml) at 22° for 1 hour and the resulting solution was cooled in an ice/salt bath to −10°. A solution of Intermediate 30 (0.8 g) in anhydrous N,N-dimethylformamide (6 ml) was added and the solution was stirred for 45 min. Water (75 ml) was added and the mixture was extracted with ethyl acetate (2×100 ml). The combined organic layers were washed successively with 50 ml each of 2N hydrochloric acid (2×), water, saturated aqueous sodium bicarbonate, water, 10% aqueous sodium metabisulphite, water (2×) and saturated brine, dried over magnesium sulphate and concentrated under vacuum to ca 10 ml. The solution was added dropwise to stirred petroleum ether (100 ml) to give a precipitate which was filtered off, washed with petroleum ether and dried under reduced pressure to give the ester (0.788 g), m.p. 133° (Mettler), $[\alpha]_D^{22°}$ +45° (c 1.165 in dioxan).

EXAMPLE 1

1-(2-Methoxypropionyloxy)ethyl (6R,7R)-3-Carbamoyloxymethyl-7-[(Z)-(2)-(fur-2-yl)-2-methoxyiminoacetamido]ceph-3-em-4-carboxylate To a stirred solution of cefuroxime (4.24 g) in anhydrous N,N-dimethylformamide (100 ml) at 20° was added potassium carbonate (0.69 g) followed after 10 mins by 2-methoxypropanoic acid 1-bromoethyl ester (2.11 g). The mixture was stirred for 2 hours and it was then poured into a mixture of ethyl acetate (100 ml) and 2N hydrochloric acid (100 ml). The organic phase was washed with 2N hydrochloric acid (100 ml) and the combined aqueous phases were extracted with ethyl acetate (2×50 ml). The organic layers were combined, washed sequentially with saturated aqueous sodium bicarbonate solution (100 ml), water (100 ml) and saturated brine (100 ml), dried over sodium sulphate and evaporated to give a foam (3.56 g). The crude product was purified by chromatography on silica gel (110 g) eluting with a 4 to 1 mixture of dichloromethane and acetone. Appropriate fractions were combined and evaporated to give the title ester as a white foam (2.85 g). PMR showed the presence of approximately 20% of the $\Delta^2$- isomer as a contaminant.

To a solution of the mixture of $\Delta^2$ and $\Delta^3$ isomers (4.91 g); two similar batches were combined) in dichloromethane (100 ml), stirred and cooled in ice, was added m-chloroperoxybenzoic acid (1.8 g). Dichloromethane (100 ml) was added to the resulting suspension to facilitate stirring and the mixture was stirred for 1.5 hours. More dichloromethane (100 ml) was added and the solvent was evaporated off under reduced pressure. The solid residue was triturated with ether, filtered off, washed with ether and dried under vacuum to give the β-sulphoxide derivative of the title compound as a white solid (3.99 g), $[\alpha]_D^{22°}$ +67° (c 0.903 in DMSO), $\lambda_{max}^{EtOH}$ 276.5 mm E$_1^1$ 307.

To a solution of the sulphoxide (3.768 g) in anhydrous N,N-dimethylformamide (100 ml) cooled in ice were added potassium iodide (4.39 g) and acetyl chloride (0.94 ml) and the mixture was stirred at 0° for 1 hour. The reaction mixture was partitioned between ethyl acetate (100 ml) and aqueous sodium metabisulphite solution (100 ml) and the organic layer was washed with aqueous sodium metabisulphite solution (100 ml). The combined aqueous phases were extracted with ethyl acetate (2×50 ml) and the organic layers were combined, washed sequentially with 2N hydrochloric acid (100 ml), water (100 ml), and saturated brine (100 ml), dried over sodium sulphate and evaporated under reduced pressure to give a yellow solid (4.02 g). The crude product was dissolved in dichloromethane (20 ml), insoluble material (ca 400 mg) was filtered off, and the filtrate was adsorbed onto a column of silica gel 60 (110 g). The column was eluted with a 3 to 1 mixture of dichloromethane and acetone and appropriate fractions were combined and evaporated under vacuum to give the cefuroxime ester as a pale yellow foam (2.99 g), $[\alpha]_D$+35° (c 1.445 in chloroform), $\lambda_{max}^{EtOH}$ 277 nm E$_1^1$ 344.

The compounds listed in Table 1 were prepared in a similar manner with the following exceptions.

EXAMPLE 3

Twice the number of molar equivalents of potassium iodide and acetyl chloride were used. The final product was not chromatographed but was precipitated from dichloromethane and petrol. Cefuroxime sodium salt was used in place of cefuroxime and potassium carbonate.

EXAMPLE 4

The mixture of $\Delta^2$ and $\Delta^3$ isomers was not chromatographed; both it and the final product were precipitated from ethyl acetate by addition of the solution to petrol. The reduction reaction mixture was partitioned between ethyl acetate and 2N hydrochloric acid.

EXAMPLE 5

Cefuroxime sodium salt was used instead of cefuroxime and potassium carbonate. Neither the $\Delta^2/\Delta^3$ mixture nor the final product was chromatographed; both were precipitated from dichloromethane by addition of the solution to petrol. Twice the number of molar equivalents of acetyl chloride and potassium iodide were used in the reduction of the sulphoxide.

TABLE 1

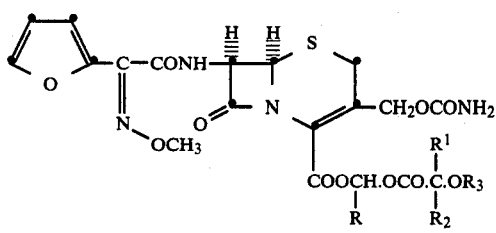

| Example No. | R | R₁ | R₂ | R₃ | M | Molar equiv. of alkylating agent | Reaction Time (hrs) | Reaction Temp (°C.) |
|---|---|---|---|---|---|---|---|---|
| 2 | $CH_3$ | H | $CH_3$ | $CH_3$ | K | 1.0 | 2 | 20° |
| 3 | $CH_3$ | H | H | $CH_2CH_3$ | Na | 1.8 | 16 | 22° |
| 4[1][2] | $CH_3$ | H | H | $C(CH_3)_3$ | K | 0.95 | 67 | 22° |
| 5 | $CH(CH_3)_2$ | H | H | $CH_2CH_3$ | Na | 0.84 | 16 | 22° |

[2]Alkylation with a chloro- compound
[1]Purified by chromatography

| | $\lambda_{max}$ (nm) | | $E_1^1$ | | $\nu_{max}$ (Nujol) | | | |
|---|---|---|---|---|---|---|---|---|
| | | | | | β-lactum | | Ester carbamate | |
| Example No. | S=O; (CHCl₃) | S (EtOH) | S=O; | S | S=O; | S | S=O; | S |
| 2 | 276.5 (EtOH) | 277 | 307 | 344 | 1790 | 1788 | 1770 1730 1698 | 1754 1736 |
| 3 | 278 | 277.5 | 170 | 347 | 1785 | 1780 | 1770 1695 | 1780 1730 |
| 4 | 279 | 277.5 | 263 | 328 | 1790 | 1784 | 1735 1700 | 1754 1732 |
| 5* | 279.5 | 277 | 262 | 338 | 1792 | 1780 | 1780 1730 1702 | 1780 1732 |

*The infra red spectrum of the final sulphide compound was obtained using bromoform rather than Nujol.

EXAMPLE 6

(R and S) (2-Methoxy-2-methyl-propionyloxy)methyl (6R,7R)-3-Carbamoyloxymethyl-7-[(Z)-2-(fur-2-yl)-2-methoxyiminoacetamido]ceph-3-em-4-carboxylate Cefuroxime (1.697 g) and powdered potassium carbonate (276 mg) were stirred in anhydrous N,N-dimethylformamide (20 ml) at 22° for 1 hour and the resulting solution was cooled in an ice/salt bath to −8°. A solution of crude 2-methoxy-2-methylpropanoic acid iodomethyl ester (1.52 g) in anhydrous N,N-dimethylformamide (6 ml) was added and the solution was stirred for 35 mins. Water (75 ml) was added and the mixture was extracted with ethyl acetate (2×100 ml). The combined organic layers were washed successively with 50 ml each of 2N hydrochloric acid (3×), water, saturated aqueous sodium bicarbonate, water, 10% aqueous sodium metabisulphite, water (2×) and saturated brine, dried over magnesium sulphate and concentrated under vacuum to ca 10 ml. The solution was added dropwise to stirred petroleum ether (100 ml) to give a precipitate which was filtered off, washed with petroleum ether and dried under reduced pressure to give the title ester (1.532 g); $\lambda_{max}$ (ethanol 277) nm $E_1^1$ 323; $\nu_{max}$ (CHBr₃) 3520 and 3400 (NH and NH₂), 1788 (β-lactam C=O); 1735 (ester and carbamate C=O) and 1685 and 1510 cm⁻¹ (amide C=O).

EXAMPLE 7

(R and S) 1-(2-Methoxy-2-methylpropionyloxy)ethyl (6R,7R)-3-Carbamoyloxymethyl-7-[(Z)-2-(fur-2-yl)-methoxyiminoacetamido]ceph-3-em-4-carboxylate Cefuroxime (4.24 g) and powdered potassium carbonate (0.690 g) were stirred in anhydrous N,N-dimethylformamide (40 ml) till a solution was obtained. The solution was cooled to −3°, 2-methoxy-2-methylpropanoic acid 1-bromoethyl ester (2.50 g) was added and the solution was stirred for 1 hour. It was then partitioned between 2N hydrochloric acid (100 ml) and ethyl acetate (200 ml and 100 ml) and the combined organic layers were washed sequentially with 100 ml each of 2N hydrochloric acid (2×), water, saturated aqueous sodium bicarbonate, water (2×) and saturated brine, dried over magnesium sulphate and concentrated under reduced pressure to ca 20 ml. The solution was added slowly to petroleum ether (200 ml) and the resulting precipitate was filtered off, washed with petroleum ether and dried under vacuum to give the title ester (2.20 g); $\lambda_{max}$ (ethanol) 277.5 nm $E_1^1$ 342; $\nu_{max}$ (CHBr₃) 3520 and 3400 (NH and NH₂), 1788 (β-lactam C=O), 1750 (ester C=O), 1732 (αβ unsaturated ester and carbamate C=O), and 1688 and 1514 cm⁻¹ (amide C=O).

EXAMPLE 8

(R and S) 1-(2-Methoxy-2-methylpropionyloxy)ethyl (6R,7R)-3-Carbamoyloxymethyl-7-[(Z)-2-(fur-2-yl)-2-methoxyiminoacetamido]ceph-3-em-4-carboxylate A solution of Intermediate 13 (1.085 g) and (Z)-2-(fur-2-yl)-2-methoxyimino acetic acid (463 mg) in dichloromethane was stirred at 20° with dicyclohexylcarbodiimide (632 mg) for 1 h. The mixture was treated with acetic acid (2 drops), filtered, evaporated, and partitioned between ethyl acetate (100 ml) and saturated sodium bicarbonate solution (30 ml). The organic layer was washed with water, then brine and was dried and evaporated to give a foam (1.74 g). This foam was stirred with dichloromethane, filtered, concentrated, and the solution was loaded on a column (4 cm dia × 14 cm) of silica (80 g) made up in dichloromethane-ethyl acetate (3:1). The fractions eluted with dichloromethane-ethyl acetate (3:1) were discarded. Dichloromethane-ethyl acetate (3:2) eluted fractions were concentrated and added to petroleum ether to give the title compound as a solid (191 mg), $[\alpha]_D^{22}+47°$, $\lambda_{max}$ 277 nm ($E_1^1$ 338).

EXAMPLE 9

(R and S) 1-(2-Methoxy-2-methylpropionyloxy)ethyl (6R,7R)-3-Carbamoyloxymethyl-7-[(Z)-2-(fur-2-yl)-2-methoxyiminoacetamido]ceph-3-em-4-carboxylate A solution of Intermediate 15 [in dimethylformamide (100 ml)] was treated dropwise with stirring under nitrogen with chlorosulphonyl isocyanate (1.691 g), and stirred at 0° for 20 min. The solution was then poured onto a stirred mixture of ice (200 l g), 2M-hydrochloric acid (200 ml) and ethyl acetate (200 ml), and stirred for 30 min. The 2 layers were separated and the aqueous layer was extracted with ethyl acetate (200 ml). The combined organic layers were washed with water (2×200 ml) and brine (2×50 ml) and the solution was dried and concentrated to 30 ml. This was added to petroleum ether to give the title compound as a solid (959 mg), $\lambda_{max}$ 275 nm ($E_1^1$ 383). The combined aqueous layers from above were stirred at 20° for 2 h and similarly extracted and precipitated to give a similar second crop (373 mg). The two crops were combined and most (1.198 g) was dissolved in ethyl acetate, the solution filtered. The filtrate was adsorbed on silica gel (12 g) and chromatographed on a column (4 cm dia × 10 cm) of silica gel (60 g) eluting with dichloromethane-ethyl acetate (3:1), followed by dichloromethane-ethyl acetate (3:2) and the fractions discarded. The column was then eluted with dichloromethane- ethyl acetate (1:1) and the fractions were combined, concentrated, and added to petroleum ether to give the title compound (300 mg) as a solid $[\alpha]_D^{20}+66°$, $\lambda_{max}$ 277 nm ($E_1^1$ 343).

EXAMPLE 10

(R and S) 1-(2-Methoxy-2-methylpropionyloxy)ethyl (6R,7R)-3-Carbamoyloxymethyl-7-[(Z)-2-(fur-2-yl)-2-methoxyiminoacetamido]ceph-3-em-4-carboxylate.

Method (i)

A solution of sodium formate (150 mg) in water (2 ml) was added to a stirred solution of Intermediate 16 (719 mg) in methanol (15 ml) at 20°. After 3.5 h more sodium formate (51 mg) was added. The solution was stirred for a further 1 hour, was evaporated and partitioned between sodium bicarbonate (20 ml) and ethyl acetate (100 ml). The aqueous layer was extracted with ethyl acetate and the organic layers were combined, washed with water (2×50 ml), brine (2×30 ml), dried, concentrated and added to petroleum ether to give the carbamate as a solid (317 mg). Most (302 mg) of this solid was dissolved in dichloromethane and chromatographed on a column (2 cm dia × 9 cm) of silica (15 g). The column was eluted with dichloromethane-ethyl acetate (3:1) and the fractions discarded. The column was then eluted with dichloromethane-ethyl acetate (3:2) and the fractions were combined, concentrated, and added to petroleum ether to give the title compound as a solid (86 mg), $[\alpha]_D^{22}+95°$, $\mu_{max}$ 277 nm ($E_1^1$ 332).

Method (ii)

Intermediate 16 (409 mg) was adsorbed on silica (4 g) and chromatographed on a column (2.5 cm dia × 8 cm) of silica (20 g) in dichloromethane-ethyl acetate (3:1). The column was eluted with dichloromethane-ethyl acetate (3:1) and the fractions discarded. This was followed by elution with dichloromethane-ethyl acetate (3:2) and the fractions were combined, concentrated, and added to petroleum ether to give the title compound as a solid (68 mg), $[\alpha]_D^{20}+80°$, $\lambda_{max}$ 277 nm ($E_1^1$ 345).

EXAMPLE 11

(R and S)1-(2-Methoxy-2-methylpropionyloxy)ethyl (6R,7R)-3-Carbamoyloxymethyl-7-[(Z)-2-(fur-2-yl)-2-methoxyiminoacetamido]ceph-3-em-4-carboxylate

(i) By reduction of the sulphoxide

A solution of Intermediate 23 (0.500 g) in dimethylformamide (15 ml) was stirred with potassium iodide (1.14 g) at 0° for 15 min. It was cooled to −15° and stirred with acetyl chloride (0.24 ml) at −15° for 15 min, then at −5° for 10 min. The solution was added to 10% aqueous sodium metabisulphite to give a precipitate which was filtered off washed and dried to give a gum. The aqueous filtrate was extracted with ethyl acetate (2×30 ml) which was used to dissolve the gum. The ethyl acetate solution was washed with water (2×30 ml) then brine (50 ml), and was dried over magnesium sulphate and concentrated to ca. 5 ml. This solution was added to pertroleum ether to give the title compound as a solid (0.368 g), $[\alpha]_D^{26}+16°$, $\lambda_{max}$ 276 nm ($E_1^1$ 338).

(ii) By isomerisation

A solution of Intermediate 22 (containing ca. 10% of the $\Delta^3$ isomer: 112 mg) in ethyl acetate (5 ml) was stirred with triethylamine (0.15 ml) at 20° for 2 h by when the optical rotation had stopped dropping. The solution was washed with 2M-hydrochloric acid, water and brine. It was dried and concentrated and added to petroleum ether to give a solid (16 mg) and a filrate which was evaporated to a gum (105 mg). The solid and gum both contained ca. 35% of the $\Delta^3$ isomer by h.p.l.i. A similar mixture (1.445 g) was chromatographed on a column (4.5 cm dia. × 14 cm) of silica (100 g) eluting initially with dichloromethane-ethyl acetate (3:1). Dichloromethane-ethyl acetate (2:1) eluted a solution which was concentrated and added to petroleum ether to give the title compound as a solid (118 mg), $[\alpha]_D^{21}+103°$, $\lambda_{max}$ 277.5 nm ($E_1^1$ 333).

EXAMPLE 12

(R and S) 1-(2-Methoxy-2-methylpropionyloxy)ethyl (6R,7R)-3-Carbamoyloxymethyl-7-[(Z)-2-(fur-2-yl)-2-methoxyiminoacetamido]ceph-3-em-4-carboxylate A mixture of Intermediate 26 (500 mg) and methoxyamine hydrochloride (93 mg) was stirred in ethanol (10 ml) at ca. 0°. Dimethylformamide was added dropwise until a clear solution was obtained. Pyridine (0.12 ml) was added and the reaction mixture was stirred at 0° to 4° for 26 hr. Methoxyamine hydrochloride (93 mg) and pyridine (0.12 ml) were added and the reaction mixture was stirred at 0° to 4° and at pH 5.3 for a further 5 h. Methoxyamine hydrochloride (93 mg) was added and the pH adjusted to 4.2 with 2M-hydrochloric acid. The reaction mixture was stirred at 0° to 4° for a further 19 h, then partitioned between ethyl acetate (50 ml) and 2M-hydrochloric acid (50 ml). The aqueous layer was extracted with ethyl acetate (2×30 ml), and the organic layers were combined, washed with water (50 ml), saturated sodium bicarbonate solution (30 ml) and brine (50 ml). The solution was dried over magnesium sulphate and evaporated to give an oil. This oil was dissolved in ethyl acetate (5 ml) and the solution was added to petroleum ether (50 ml) to give as a solid (270 mg) a mixture containing the title compound, $\lambda_{max}$ 282 nm ($E_1^1$ 282), $\nu_{max}$ (Nujol) 3700 to 3100 ($NH_2$ NH), 1782 ($\beta$-lactam), 1750 and 1730 ($-CO_2R$ and $-OCONH_2$), 1663 and 1516 cm$^{-1}$ (CONH).

EXAMPLE 13

(R and S) 1-(2-Methoxy-2-methylpropionyloxy)ethyl (6R,7R)-3-Carbamoyloxymethyl-7-[(Z)-2-(fur-2-yl)-2-methoxyiminoacetamido]ceph-3-em-4-carboxylate A solution of Intermediate 28 (0.300 g) in ethyl acetate (10 ml) was stirred with a solution of diazomethane (excess) in ether (ca. 20 ml) at 22° for 4 h. The solution was cooled to ca. 0°, stirred with acetic acid (excess), diluted with ethyl acetate (30 ml), and washed with water (30 ml), saturated sodium bicarbonate solution (30 ml), water (30 ml), and brine (30 ml), and was dried over magnesium sulphate. The solution was concentrated to ca. 5 ml and added to petroleum ether (30 ml) to give a solid (207 mg). Part (200 mg) of this solid was chromatographed on two Whatman 20×20 cm PK 6F silica plates, which were developed with dichloromethane-ethyl acetate (3:2). The appropriate band was removed and eluted with ethyl acetate, which was evaporated to give the title compund as a foam (19 mg). The spectral characteristics of which resembled those of the product of Example 7.

EXAMPLE 14

(R and S)-1-(2-Methoxy-2-methylpropionyloxy)ethyl (6R,7R)-3-Carbamoyloxymethyl-7-[(Z)-2-(fur-2-yl)-2-methoxyiminoacetamido]ceph-3-em-4-carboxylate A solution of Intermediate 18 (101 mg) in acetonitrile (120 ml) was irradiated at ca. 20° by a Hanan high-pressure Z1 125 watt mercury vapour lamp through pyrex for 45 mins. The solution was evaporated and the gum was dissolved in ethyl acetate (2 ml) which was added to petroleum ether (40 ml) to give the title compound as a solid (71 mg), $\lambda_{max}$ 276 nm ($E_1^1$ 293).

EXAMPLE 15

(R and S) 1-(2-Methoxy-2-methylpropionyloxy)ethyl (6R,7R)-3-carbamoyloxymethyl-7-[(Z)-2-(fur-2-yl)-2-methoxyiminoacetamido]ceph-3-em-4-carboxylate A solution of sodium iodide (69.8 g) in acetone (260 ml) at 20° was treated with Intermediate 7 (65.5 g). The mixture was stirred for 20 minutes at 20° then petroleum ether (bp 60°-80°, 460 ml) and a solution of sodium bicarbonate (13.1 g) and sodium chloride (100 g) in water (660 ml) were added. The layers were separated and the upper layer was washed with a solution of sodium bicarbonate (13.1 g) and sodium chloride (100 g) in water (660 ml). Meanwhile cefuroxime sodium salt (100 g) was stirred with N,N'-dimethylacetamide (520 ml). The resulting solution was cooled to 0° then treated with the organic phase from the above, washed in with N,N'-dimethylacetamido (50 ml), and stirred 1 hour at 5° to 8°. It was then treated with a solution of sodium sulphite (5.6 g) and sodium metabisulphite (8.5 g) in water (380 ml). The mixture was stirred during 90 minutes at a pH between 6.5 and 5.3. The layers were separated and the lower phase was added during 15 minutes to stirred water (5700 ml). The resultant suspension was stirred and cooled to 12° over 60 minutes. Collection by filtration, washing with water and drying in vacuo gave the title compound (100.9 g) having similar spectral characteristics to the product of Example 7.

EXAMPLE 16

(R and S) 1-(2-Methoxy-2-methylpropionyloxy)ethyl (6R,7R)-3-carbamoyloxymethyl-7-[(Z)-2-(fur-2-yl)-2-methoxyiminoacetamido]ceph-3-em-4-carboxylate The 1-(-2-methoxy-2-methylpropionyloxy)ethyl ester of cefuroxime was dissolved in methanol (350 ml) and treated with activated charcoal (5 g). The charcoal was removed by filtration through Kieselguhr and the bed was washed with methanol (50 ml). The combined filtrate and wash were added to water (1000 ml) stirred at 20° during 20 minutes, then the resultant suspension was cooled to 10°. Filtration, washing with water and drying in vacuo gave the title ester (78.1 g) as a substantially pure, amorphous solid having similar spectral characteristics to the product of Example 7.

EXAMPLE 17

(2-Methoxy-2-methylpropionyloxy)methyl (6R,7R)-3-Carbamoyloxymethyl-7-[(Z)-2-(fur-2-yl)-2-methoxyiminoacetamido]ceph-3-em-4-carboxylate A solution of Intermediate 31 (81 mg) in dichloromethane (10 ml) was stirred at ca. 20° with a solution of diazomethane (excess) in ether (10 ml). Boron trifluoride etherate (1 drop) was added and then more (10 ml) of the diazomethane solution. The mixture was stirred at 20° for 1 h then stirred with acetic acid (1 ml), ethyl acetate and water. The aqueous layer was separated and extracted with ethyl acetate. The organic layers were combined, washed with water (3×), brine (2×), dried and evaporated to a gum. This gum was dissolved in ethyl acetate (2 ml), which was added to petroleum ether (40 ml) to give the title compound as a solid (34 mg), $\lambda_{max}$ 276 nm ($E_1^1$ 354). I.R. and n.m.r. spectra resembled those of the product of Example 7.

PHARMACY EXAMPLES

| Example A | mg/tablet |
|---|---|
| Cefuroxime 1-(2-methoxy-2-methyl-propionyloxy) ethyl ester equivalent to 250 mg cefuroxime | 334 |
| Microcrystalline cellulose | 31 |
| Croscarmellose sodium | 40 |
| Sodium lauryl sulphate | 10 |
| Hydrogenated vegetable oil | 2 |
| Silicon dioxide | 3 |
| Polyvinyl pyrrolidone | 5 |
| Tablet | 425 mg |

The cefuroxime ester was sieved through a 100 mesh screen. It was then blended with the microcrystalline cellulose, silicon dioxide, sodium lauryl sulphate and half the croscarmellose sodium. An aqueous solution of the polyvinyl pyrrolidone (1.5% w/v) was prepared. This solution was then added to the powder blend in a mixer. It was necessary to add a further volume of water (0.14% of the PVP solution) for granulation. The granulate was then passed through a 20 mesh screen. The granules were then dried at 35°–40° C. in an oven. The dry granules were then mixed with the remaining excipients which had previously been passed through a 36 mesh screen. The material was compressed on a F machine with capsule shaped punches.

| Example B | mg/tablet |
|---|---|
| Cefuroxime 1-(2-methoxy-2-methyl-propionyloxy) ethyl ester equivalent to 250 mg cefuroxime | 334 |
| Croscarmellose sodium | 43 |
| Sodium lauryl sulphate | 5 |
| Hydrogenated vegetable oil | 5 |
| Microcrystalline cellulose | 36.9375 |
| Silicon dioxide | 1.0625 |
| Tablet | 425 mg |

The cefuroxime ester was sieved through a 100 mesh screen. It was then blended with the croscarmellose sodium, sodium lauryl sulphate, hydrogenated vegetable oil and microcrystalline cellulose. The silicon dioxide was sieved through a 60 mesh screen together with some of the blend. This was placed in a cube blender with the rest of the blend and mixing continued for a further ten minutes. The material was compressed on an F machine with a 7/16 bevel edged tablet punch.

| Example C | mg/capsule |
|---|---|
| Cefuroxime 1-(2-methoxy-2-methylpropionyloxy) ethyl ester equivalent to 250 mg cefuroxime | 335 |
| Microcrystalline cellulose | 41.5 |
| Croscarmellose sodium | 20 |
| Sodium bicarbonate | 22.7 |
| Anhydrous citric acid | 17.3 |
| Sodium lauryl sulphate | 10 |
| Hydrogenated vegetable oil | 1.5 |
| Silicon dioxide | 2 |
| Total weight | 450 mg |

The cefuroxime ester was sieved through a 100 mesh screen. All the other excipients except the hydrogenated vegetable oil and the anhydrous citric acid were blended together and then passed through a 100 mesh screen. The blend and the cefuroxime ester were then mixed with the citric acid which had previously been passed through a 60 mesh screen. This material was then passed through a mikropulveriser fitted with an 8 inch wheel and a herringbone screen. The resultant blend was then passed through a 20 mesh screen. The required quantity of hydrogenated vegetable oil was sieved through a 20 mesh screen and mixed with the blend. This material was filled into size 0 hard gelatin capsules on a Zanasi LZ64 machine.

| Example D | mg/dose |
|---|---|
| Cefuroxime 1-(2-methoxy-2-methyl)propionyloxyethyl ester equivalent to 125 mg cefuroxime | 167.7 |
| Sodium Carboxymethylcellulose | 40 |
| Powdered sugar | 3000 |
| Flavour | 5.0–70.0 |

The cefuroxime ester was sieved through a 100 mesh screen and the powdered sugar through a 30 mesh screen. The cefuroxime ester was then blended with the sodium carboxymethylcellulose and the powdered sugar.

The power blend was then granulated using an aqueous solution of 0.08% sodium lauryl sulphate and the flavour added.

| Example E | mg/dose |
|---|---|
| Cefuroxime (2-methoxy-2-methyl)propionyloxymethyl ester equivalent to 250 mg cefuroxime | 327 |
| Sodium starch glycollate | 6 |
| Microcrystalline cellulose | 65 |
| Magnesium stearate | 2 |
| Tablet weight | 400 mg |

The magnesium stearate is blended with the cefuroxime ester and tablet slugs prepared by direct compression. These are broken down through 12 mesh, 16 mesh and 20 mesh screens consecutively then the granules are blended with the sodium starch glycollate and microcrystalline cellulose. Compress on appropriate punches on an automatic tablet press. The tablets may be covered in a thin polymer coat applied by the usual film coating techniques. A pigment may be included in the film coat.

We claim:

1. Compounds of the formula (I)

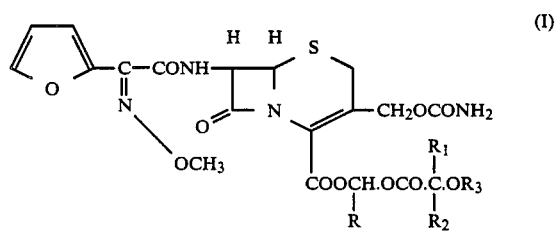

wherein R, R$_1$ and R$_2$, which may be the same or different, each represents a hydrogen atom or a C$_{1-4}$ alkyl group and R$_3$ represents a C$_{1-4}$ alkyl group, with the proviso that, when both R$_1$ and R$_2$ represent hydrogen atoms, R$_3$ represents other than a methyl group.

2. Compounds according to claim 1 wherein R represents a hydrogen atom or a methyl group, R$_1$ and R$_2$ each represents a methyl group and R$_3$ represents a C$_{1-4}$ alkyl group.

3. (R and S) 1-(2-Methoxy-2-methylpropionyloxy)ethyl (6R,7R)-3-carbamoyloxymethyl-7-[(Z)-2-(fur-2-yl)-2-methoxyiminoacetamido]ceph-3-em-4-carboxylate and diastereoisomeric mixtures thereof.

4. (2-Methoxy-2-methylpropionyloxy)methyl (6, 7R)-3-carbamoyloxymethyl-7-[(Z)-2-(fur-2-yl)-2-methoxyiminoacetamido]ceph-3-em-4-carboxylate.

5. Compounds according to claim 1 in substantially amorphous form.

6. Antibacterial pharmaceutical compositions for oral administration comprising an antibacterial effective amount of a compound according to claim 1 in association with at least one pharmaceutical carrier or excipient.

7. A method of combating bacterial infections of the human or animal body which comprises orally administering thereto an effective amount of a compound of formula (I) as defined in claim 1.

* * * * *